(12) United States Patent
Dunia et al.

(10) Patent No.: US 10,059,748 B2
(45) Date of Patent: Aug. 28, 2018

(54) PHARMACEUTICAL COMPOSITIONS FOR PREVENTION OR TREATMENT OF NEURODEGENERATIVE DISEASES

(71) Applicants: INSERM (INSTITUT NATIONAL DE LA SANTÉ ET DE LA RECHERCHE MÉDICALE), Paris (FR); UNIVERSITÉ PAUL SABATIER TOULOUSE III, Toulouse (FR); CENTRE NATIONAL DE LA RECHERCHE SCIENTIFIQUE (CNRS), Paris (FR); UNIVERSITÉ PIERRE ET MARIE CURIE (PARIS 6), Paris (FR); ICM (INSTITUT DU CERVEAU ET DE LA MOELLE EPINIERE), Paris (FR)

(72) Inventors: Daniel Dunia, Toulouse (FR); Marion Szelechowski, Toulouse (FR); Alexandre Betourne, San Francisco, CA (US); Stephane Hunot, Paris (FR)

(73) Assignees: INSERM (INSTITUT NATIONAL DE LA SANTÉ ET DE LA RECHERCHE MÉDICALE), Paris (FR); UNIVERSITÉ PAUL SABATIER TOULOUSE III, Toulouse (FR); CENTRE NATIONAL DE LA RECHERCHE SCIENTIFIQUE (CNRS), Paris (FR); UNIVERSITÉ PIERRE ET MARIE CURIE (PARIS 6), Paris (FR); ICM (INSTITUT DU CERVEAU ET DE LA MOELLE EPINIERE), Paris (FR)

( * ) Notice: Subject to any disclaimer, the term of this patent is extended or adjusted under 35 U.S.C. 154(b) by 0 days.

(21) Appl. No.: 15/317,196

(22) PCT Filed: Jun. 8, 2015

(86) PCT No.: PCT/EP2015/062651
§ 371 (c)(1),
(2) Date: Dec. 8, 2016

(87) PCT Pub. No.: WO2015/189116
PCT Pub. Date: Dec. 17, 2016

(65) Prior Publication Data
US 2017/0137472 A1 May 18, 2017

Related U.S. Application Data

(60) Provisional application No. 62/062,370, filed on Oct. 10, 2014.

(30) Foreign Application Priority Data

Jun. 10, 2014 (EP) .................................. 14305874

(51) Int. Cl.
A61K 38/00 (2006.01)
C07K 14/005 (2006.01)
A61K 38/16 (2006.01)
C12N 7/00 (2006.01)

(52) U.S. Cl.
CPC .......... *C07K 14/005* (2013.01); *A61K 38/162* (2013.01); *C12N 7/00* (2013.01); *C07K 2319/07* (2013.01); *C07K 2319/10* (2013.01); *C12N 2740/16322* (2013.01); *C12N 2760/00022* (2013.01); *C12N 2760/00033* (2013.01)

(58) Field of Classification Search
None
See application file for complete search history.

(56) References Cited

U.S. PATENT DOCUMENTS 6,740,486 B1 * 5/2004 Lai ....................... C07K 14/005
435/320.1

FOREIGN PATENT DOCUMENTS

WO 00/12548 A1 3/2000

OTHER PUBLICATIONS

Nishino et al. (J Virol. Sep. 2002;76(17):8650-8) (Year: 2002).*
GenBank AAM68135.1 (downloaded online on Dec. 7, 2017 from URL:<https://www.ncbi.nlm.nih.gov/protein/22265339?report=genbank&log$=protalign&blast_rank=3&RID=2JAT4K0A01R>) (Year: 2017).*
Poenisch Marion et al: "Protein X of Borna Disease Virus Inhibits Apoptosis and Promotes Viral Persistence in the Central Nervous Systems of Newborn-Infected Rats", Journal of Virology, vol. 83, No. 9, pp. 4297-4307, May 2009.
Hashimoto Yoshio et al: "Two major histocompatibility complex I-restricted epitopes of the Borna disease virus p10 protein identified by cytotoxic T lymphocytes induced by DNA-based immunization.", Journal of Virology, vol. 77, No. 10, pp. 6076-6081, May 2003.
Szelechowski Marion et al: "A viral peptide that targets mitochondria protects against neuronal degeneration in models of Parkinson's disease." Nature Communications, vol. 5, 5181, pp. 1-12, Oct. 21, 2014.

* cited by examiner

*Primary Examiner* — Jennifer Pitrak McDonald
*Assistant Examiner* — Sergio Coffa
(74) *Attorney, Agent, or Firm* — W&C IP

(57) ABSTRACT

The present invention relates to methods and compositions for the prevention or treatment of neurodegenerative diseases.

Figure 1:
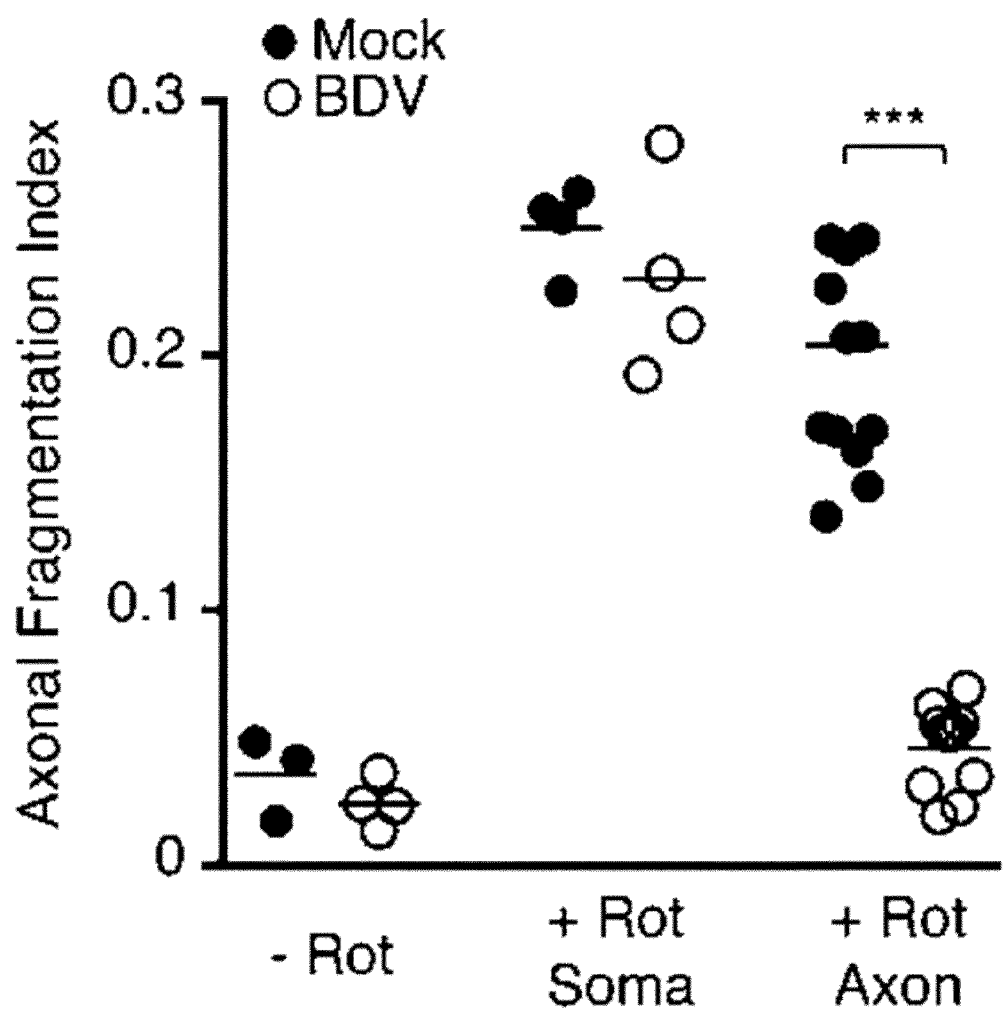

13 Claims, 11 Drawing Sheets
Specification includes a Sequence Listing.

Figure 2

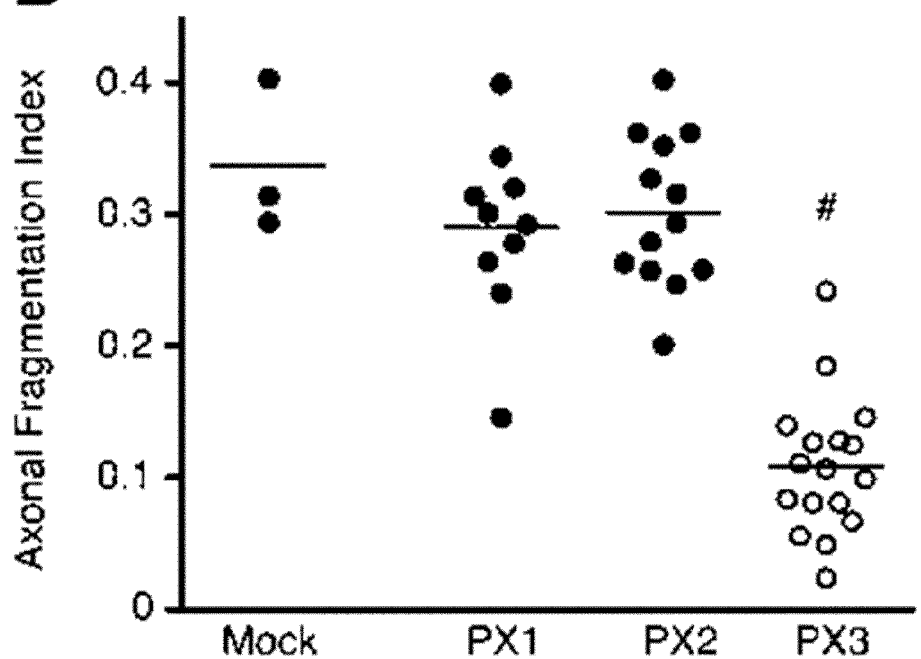
Figure 4 A-B

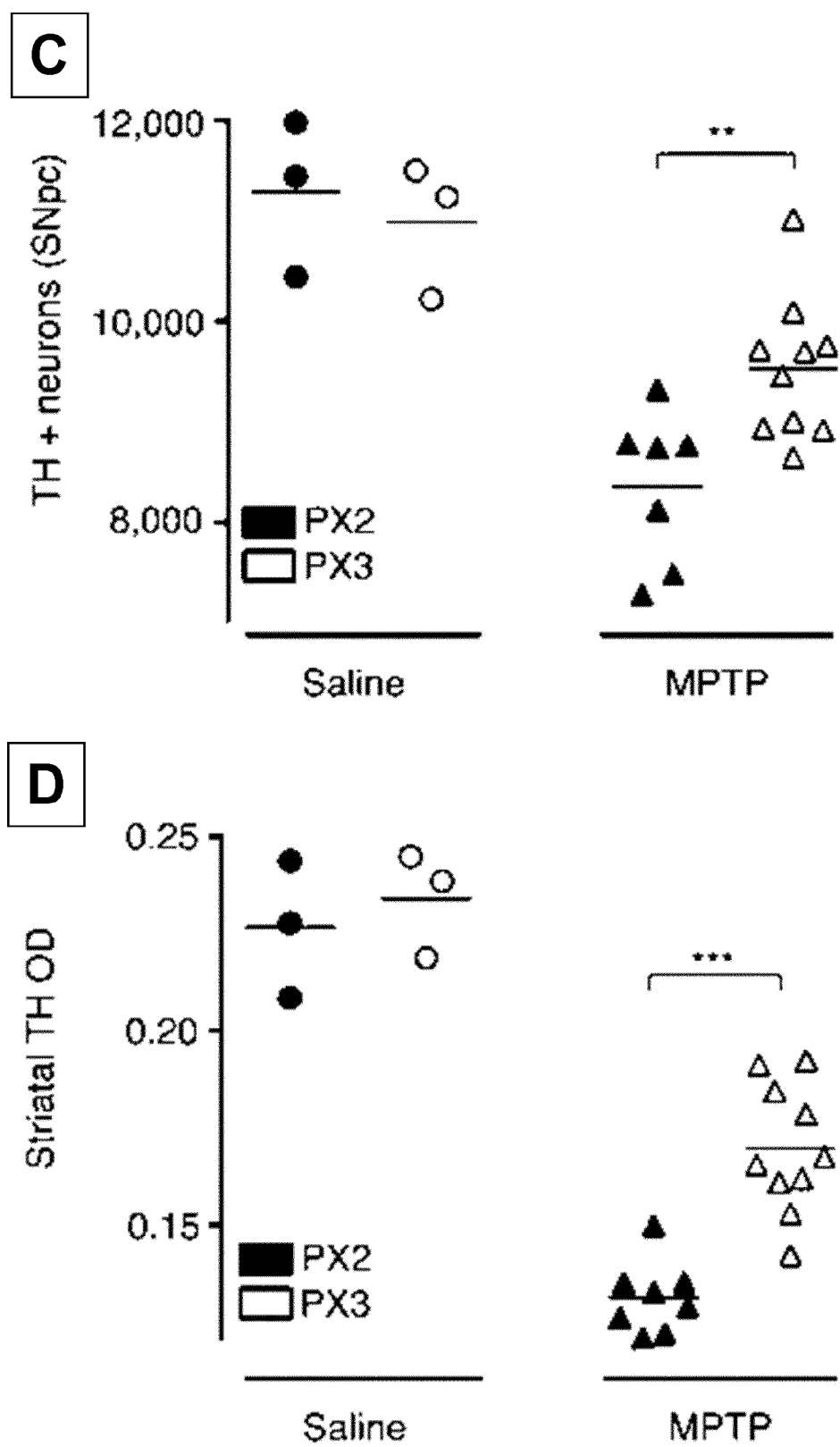
Figure 4 C-D

Figure 9

PHARMACEUTICAL COMPOSITIONS FOR PREVENTION OR TREATMENT OF NEURODEGENERATIVE DISEASES

FIELD OF THE INVENTION

The present invention relates to methods and compositions for the prevention or treatment of neurodegenerative diseases.

BACKGROUND OF THE INVENTION

Neurodegenerative diseases represent a significant human, societal and economic burden. This term includes brain diseases such as Alzheimer's disease (AD), Parkinson's disease (PD) or Amyotrophic Lateral Sclerosis (ALS). PD, the second most common neurodegenerative disease in older adults, affects more than 6.3 million people worldwide. Neurodegenerative diseases are characterized by progressive degeneration of neurons in specific functional systems of the central nervous system, such as death of dopaminergic neurons in PD. The progressive loss of structure and function of neurons in neurodegenerative diseases, such as PD, involves mitochondrial dysfunction and axonal degeneration (1, 2).

Despite considerable efforts, we still lack efficient therapies to block neuronal demise in the early stages of neurodegeneration. Accordingly, there is an urgent need to develop new approaches and drugs that will be suitable for effective and efficient treatment of neurodegenerative disorders and which could significantly retard disease progression. In this way, it has been suggested that characterization of new therapeutic compounds in neurodegenerative disorders inducing protection of neurons from degeneration associated with the preservation of mitochondrial functions and enhanced mitochondrial filamentation may be highly desirable.

Viruses, as obligatory parasites, have evolved highly specific means to hijack cellular pathways. In order to optimize the survival in their host, many viruses express proteins, or non-coding RNA, that block or delay the death of infected cells by acting at the mitochondrial level (3-5). In particular, some neurotropic viruses have very efficient strategies to protect neurons, given that their target cells have a very poor capacity of renewal. A case in point is Bornavirus (or BDV), a highly neurotropic RNA virus that persists in the brain of many animal species without causing direct damage to neurons (6). BDV non-cytolytic replication is due to the expression of an 87 amino acids viral protein called X that targets mitochondria in the infected cells (7).

Here, the inventors investigated the possibility that the X protein could protect neurons against neurodegenerative insults, even when used outside of the viral context. In particular, the inventors assessed protection against mitochondrial respiratory complex I toxins, which induce oxidative stress and neurodegeneration in tissue culture and in animal models (8-11).

There is no disclosure in the art of protein X-derived peptide effects in neurodegenerative disorders, protection of neurons from degeneration associated with the preservation of mitochondrial functions and enhanced mitochondrial filamentation and the use of the protein X-derived peptide in the treatment of neurodegenerative disorders, and the induction of hyperfilamentation of the mitochondrial network.

SUMMARY OF THE INVENTION

The present invention relates to methods and compositions for the prevention or treatment of neurodegenerative diseases.

DETAILED DESCRIPTION OF THE INVENTION

Mitochondrial dysfunction is a common feature of many neurodegenerative disorders, notably Parkinson's disease (PD). Consequently, agents able to protect mitochondria have strong therapeutic potential. Here, the inventors show that the X protein of Borna Disease Virus (BDV), a virus that persists in neurons without triggering cell death, protects neurons from degeneration both in tissue culture and in an animal model of PD. Neuroprotection was associated with the preservation of mitochondrial functions and enhanced mitochondrial filamentation. The inventors constructed a cell penetrating peptide derived from the X protein that displays similar neuroprotective properties both in cell culture and in the animal, after intranasal administration.

Protein X-Derived Peptides

The present invention relates to isolated, synthetic or recombinant protein X-derived polypeptides.

As used herein the term "protein X" has its general meaning in the art and refers to the X protein of Borna Disease Virus (BDV). The term "protein X" also refers to the X protein of Borna Disease Virus having the sequence set forth as SEQ ID NO: 1. The BDV protein X is deposited in the GenBank database accession number: AAB27262.1 (Uniprot Q86622).

```
for BDV protein X, AAB27262.1 (Uniprot Q86622)
                                        SEQ IN NO: 1
MSSDLRLTLLELVRRLNGNATIESGRLPGGRRRSPDTTTGTVGVTKTTED

PKECIDPTGRPAPEGPQEEPLHDLRPRPANRKGAAIE
```

The present invention relates to a polypeptide comprising or consisting of i) an amino acid sequence ranging from the glycine residue at position 59 to the alanine residue at position 85 in SEQ ID NO:1 or, ii) an amino acid sequence having at least 70% of identity with the amino acid sequence ranging from the glycine residue at position 59 to the alanine residue at position 85 in SEQ ID NO:1.

In a particular embodiment, the polypeptide comprises or consists of i) an amino acid sequence ranging from the glycine residue at position 59 to the isoleucine residue at position 86 in SEQ ID NO:1 or, ii) an amino acid sequence having at least 70% of identity with the amino acid sequence ranging from the glycine residue at position 59 to the isoleucine residue at position 86 in SEQ ID NO:1.

In a particular embodiment, the polypeptide comprises or consists of i) an amino acid sequence ranging from the glycine residue at position 59 to the glutamic acid residue at position 87 in SEQ ID NO:1 or, ii) an amino acid sequence having at least 70% of identity with the amino acid sequence ranging from the glycine residue at position 59 to the glutamic acid residue at position 87 in SEQ ID NO:1.

In a particular embodiment, the polypeptide comprises or consists of i) an amino acid sequence ranging from the threonine residue at position 58 to the alanine residue at position 85 in SEQ ID NO:1 or, ii) an amino acid sequence having at least 70% of identity with the amino acid sequence ranging from the threonine residue at position 58 to the alanine residue at position 85 in SEQ ID NO:1.

In a particular embodiment, the polypeptide comprises or consists of i) an amino acid sequence ranging from the threonine residue at position 58 to the isoleucine residue at position 86 in SEQ ID NO:1 or, ii) an amino acid sequence having at least 70% of identity with the amino acid sequence ranging from the threonine residue at position 58 to the isoleucine residue at position 86 in SEQ ID NO:1.

In a particular embodiment, the polypeptide comprises or consists of i) an amino acid sequence ranging from the threonine residue at position 58 to the glutamic acid residue at position 87 in SEQ ID NO:1 or, ii) an amino acid sequence having at least 70% of identity with the amino acid sequence ranging from the threonine residue at position 58 to the glutamic acid residue at position 87 in SEQ ID NO:1.

In a particular embodiment, the polypeptide comprises or consists of i) an amino acid sequence ranging from the proline residue at position 57 to the alanine residue at position 85 in SEQ ID NO:1 or, ii) an amino acid sequence having at least 70% of identity with the amino acid sequence ranging from the proline residue at position 57 to the alanine residue at position 85 in SEQ ID NO:1.

In a particular embodiment, the polypeptide comprises or consists of i) an amino acid sequence ranging from the proline residue at position 57 to the isoleucine residue at position 86 in SEQ ID NO:1 or, ii) an amino acid sequence having at least 70% of identity with the amino acid sequence ranging from the proline residue at position 57 to the isoleucine residue at position 86 in SEQ ID NO:1.

In a particular embodiment, the polypeptide comprises or consists of i) an amino acid sequence ranging from the proline residue at position 57 to the glutamic acid residue at position 87 in SEQ ID NO:1 or, ii) an amino acid sequence having at least 70% of identity with the amino acid sequence ranging from the proline residue at position 57 to the glutamic acid residue at position 87 in SEQ ID NO:1.

In a particular embodiment, the polypeptide comprises or consists of i) an amino acid sequence ranging from the aspartic acid residue at position 56 to the alanine residue at position 85 in SEQ ID NO:1 or, ii) an amino acid sequence having at least 70% of identity with the amino acid sequence ranging from the aspartic acid residue at position 56 to the alanine residue at position 85 in SEQ ID NO:1.

In a particular embodiment, the polypeptide comprises or consists of i) an amino acid sequence ranging from the aspartic acid residue at position 56 to the isoleucine residue at position 86 in SEQ ID NO:1 or, ii) an amino acid sequence having at least 70% of identity with the amino acid sequence ranging from the aspartic acid residue at position 56 to the isoleucine residue at position 86 in SEQ ID NO:1.

In a particular embodiment, the polypeptide comprises or consists of i) an amino acid sequence ranging from the aspartic acid residue at position 56 to the glutamic acid residue at position 87 in SEQ ID NO:1 or, ii) an amino acid sequence having at least 70% of identity with the amino acid sequence ranging from the aspartic acid residue at position 56 to the glutamic acid residue at position 87 in SEQ ID NO:1.

In a particular embodiment, the polypeptide comprises or consists of i) an amino acid sequence ranging from the isoleucine residue at position 55 to the alanine residue at position 85 in SEQ ID NO:1 or, ii) an amino acid sequence having at least 70% of identity with the amino acid sequence ranging from the isoleucine residue at position 55 to the alanine residue at position 85 in SEQ ID NO:1.

In a particular embodiment, the polypeptide comprises or consists of i) an amino acid sequence ranging from the isoleucine residue at position 55 to the isoleucine residue at position 86 in SEQ ID NO:1 or, ii) an amino acid sequence having at least 70% of identity with the amino acid sequence ranging from the isoleucine residue at position 55 to the isoleucine residue at position 86 in SEQ ID NO:1.

In a particular embodiment, the polypeptide comprises or consists of i) an amino acid sequence ranging from the isoleucine residue at position 55 to the glutamic acid residue at position 87 in SEQ ID NO:1 or, ii) an amino acid sequence having at least 70% of identity with the amino acid sequence ranging from the isoleucine residue at position 55 to the glutamic acid residue at position 87 in SEQ ID NO:1.

In a particular embodiment, the present invention relates to the polypeptide according to the invention wherein the amino acid residue at position 59 is serine and the amino acid residue at position 86 is valine.

According to the invention a first amino acid sequence having at least 70% of identity with a second amino acid sequence means that the first sequence has 70; 71; 72; 73; 74; 75; 76; 77; 78; 79; 80; 81; 82; 83; 84; 85; 86; 87; 88; 89; 90; 91; 92; 93; 94; 95; 96; 97; 98; or 99% of identity with the second amino acid sequence and conserving biological properties of said second amino acid sequence. Amino acid sequence identity is preferably determined using a suitable sequence alignment algorithm and default parameters, such as BLAST P (Karlin and Altschul, 1990). In particular the polypeptide of the invention is a functional conservative variant of the polypeptides according to the invention. As used herein the term "function-conservative variant" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Accordingly, a "function-conservative variant"

also includes a polypeptide which has at least 70% amino acid identity and which has the same or substantially similar properties or functions as the native or parent protein to which it is compared (i.e. neuroprotective properties). Functional properties of the polypeptide of the invention could typically be assessed in any functional assay as described in the EXAMPLE.

In some embodiments, the polypeptide of the invention comprises 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87 amino acids. In some embodiments, the polypeptide of the invention comprises less than 50 amino acids. In some embodiments, the polypeptide of the invention comprises less than 30 amino acids.

In a particular embodiment, the polypeptide of the invention does not consist of the amino acid sequence SEQ ID NO: 1.

In another particular embodiment, the polypeptide of the invention does not consist of a polypeptide having at least 70% of identity with the amino acid sequence SEQ ID NO: 1.

Fusion Proteins of the Invention

A further aspect of the invention relates to a fusion protein comprising the polypeptide according to the invention that is fused to at least one heterologous polypeptide.

The term "fusion protein" refers to the polypeptide derived from the protein X that is fused directly or via a spacer to at least one heterologous polypeptide.

According to the invention, the fusion protein comprises the polypeptide according to the invention that is fused either directly or via a spacer at its C-terminal end to the N-terminal end of the heterologous polypeptide, or at its N-terminal end to the C-terminal end of the heterologous polypeptide.

As used herein, the term "directly" means that the (first or last) amino acid at the terminal end (N or C-terminal end) of the polypeptide is fused to the (first or last) amino acid at the terminal end (N or C-terminal end) of the heterologous polypeptide.

In other words, in this embodiment, the last amino acid of the C-terminal end of said polypeptide is directly linked by a covalent bond to the first amino acid of the N-terminal end of said heterologous polypeptide, or the first amino acid of the N-terminal end of said polypeptide is directly linked by a covalent bond to the last amino acid of the C-terminal end of said heterologous polypeptide.

As used herein, the term "spacer" refers to a sequence of at least one amino acid that links the polypeptide of the invention to the heterologous polypeptide. Such a spacer may be useful to prevent steric hindrances.

In some embodiments, the heterologous polypeptide is a cell-penetrating peptide, a mitochondrial-penetrating peptide, a Transactivator of Transcription (TAT) cell penetrating sequence, a cell permeable peptide or a membranous penetrating sequence.

The term "cell-penetrating peptides" is well known in the art and refers to cell permeable sequences or membranous penetrating sequences such as penetratin, TAT mitochondrial penetrating sequence and compounds described in Bechara and Sagan, 2013; Jones and Sayers, 2012; Khafagy el and Morishita, 2012; and Malhi and Murthy, 2012.

In a particular embodiment, the heterologous polypeptide is the Transactivator of Transcription (TAT) cell penetrating sequence (G-R-K-K-R-Q-R-R-R-P-Q; SEQ ID NO:2) or the mitochondria-penetrating peptide sequence (F-R-X-K-F-R-X-K, X=Cha=cyclohexylalanine; SEQ ID NO:3), originally derived from the cell-penetrating HIV tat peptide.

In another embodiment, the heterologous polypeptide is a neurodegenerative therapeutic polypeptide.

The term "neurodegenerative therapeutic polypeptide" refers to any polypeptide that has anti-neurodegenerative activities (e.g., apoptosis inhibiting, growth inducing, neovascularization inducing, mitochondria protective, antioxidant, chaperone-like, etc. . . . ). Several such polypeptides are known in the art. (See. e.g., Bendavia Stealth Peptides, http://stealthpeptides.com/background).

In some embodiments, the heterologous polypeptide is a neurone targeting agent.

Neurone targeting agent includes but are not limited to antibodies directed against the Dopamine receptor, such as dopamine receptor interacting proteins or neuronal calcium sensor; acetylcholine receptors or antibodies or agents interacting with neurone membrane-bound and intracellular targets.

Polypeptides and Fusion Protein Production

The polypeptides or fusion proteins of the invention may be produced by any technique known per se in the art, such as, without limitation, any chemical, biological, genetic or enzymatic technique, either alone or in combination.

Knowing the amino acid sequence of the desired sequence, one skilled in the art can readily produce said polypeptides or fusion proteins, by standard techniques for production of amino acid sequences. For instance, they can be synthesized using well-known solid phase method, preferably using a commercially available peptide synthesis apparatus (such as that made by Applied Biosystems, Foster City, Calif.) and following the manufacturer's instructions.

Alternatively, the polypeptides or fusion proteins of the invention can be synthesized by recombinant DNA techniques as is now well-known in the art. For example, these fragments can be obtained as DNA expression products after incorporation of DNA sequences encoding the desired (poly) peptide into expression vectors and introduction of such vectors into suitable eukaryotic or prokaryotic hosts that will express the desired polypeptide, from which they can be later isolated using well-known techniques.

Polypeptides or fusion proteins of the invention can be used in an isolated (e.g., purified) form or contained in a vector, such as a membrane or lipid vesicle (e.g. a liposome or an erythrocyte).

In specific embodiments, it is contemplated that polypeptides or fusion proteins according to the invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution.

Accordingly, the polypeptide according to the invention may be a retro-inverso amino acid sequence. The term "retro-inverso amino acid sequence" relates to an isomeric form of an amino acid sequence in which the direction of the amino acid sequence is reversed and the chirality of each amino acid residue is inverted. Retro-inverso amino acid sequence of the present invention may be composed by D-amino acids assembled in the reverse order from that of the parental amino acid sequence-sequence.

In one embodiment, the polypeptide according to the present invention may be a D or L enantiomer amino acid sequence.

A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain.

For example, Pegylation is a well-established and validated approach for the modification of a range of polypeptides (Chapman, 2002). The benefits include among others: (a) markedly improved circulating half-lives in vivo due to either evasion of renal clearance as a result of the polymer increasing the apparent size of the molecule to above the glomerular filtration limit, and/or through evasion of cellular clearance mechanisms; (b) reduced antigenicity and immunogenicity of the molecule to which PEG is attached; (c) improved pharmacokinetics; (d) enhanced proteolytic resistance of the conjugated protein (Cunningham-Rundles et. al., 1992); and (e) improved thermal and mechanical stability of the PEGylated polypeptide.

Therefore, advantageously, the polypeptides of the invention may be covalently linked with one or more polyethylene glycol (PEG) group(s). One skilled in the art can select a suitable molecular mass for PEG, based on how the pegylated polypeptide will be used therapeutically by considering different factors including desired dosage, circulation time, resistance to proteolysis, immunogenicity, etc.

In one embodiment, the PEG of the invention terminates on one end with hydroxy or methoxy, i.e., X is H or CH3 ("methoxy PEG"). In addition, such a PEG can consist of one or more PEG side-chains which are linked together. PEGs with more than one PEG chain are called branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. One form of PEGs includes two PEG side-chains (PEG2) linked via the primary amino groups of a lysine (Monfardini et al., 1995).

To effect covalent attachment of PEG groups to the polypeptide, the hydroxyl end groups of the polymer molecule must be provided in activated form, i.e. with reactive functional groups (examples of which include primary amino groups, hydrazide (HZ), thiol, succinate (SUC), succinimidyl succinate (SS), succinimidyl succinamide (SSA), succinimidyl proprionate (SPA), succinimidyl carboxymethylate (SCM), benzotriazole carbonate (BTC), N-hydroxysuccinimide (NHS), aldehyde, nitrophenylcarbonate (NPC), and tresylate (TRES)). Suitable activated polymer molecules are commercially available, e.g. from Shearwater Polymers, Inc., Huntsville, Ala., USA, or from PolyMASC Pharmaceuticals plc, UK. Alternatively, the polymer molecules can be activated by conventional methods known in the art, e.g. as disclosed in WO 90/13540. Specific examples of activated linear or branched polymer molecules for use in the present invention are described in the Shearwater Polymers, Inc. 1997 and 2000 Catalogs (Functionalized Biocompatible Polymers for Research and pharmaceuticals, Polyethylene Glycol and Derivatives, incorporated herein by reference). Specific examples of activated PEG polymers include the following linear PEGs:NHS-PEG (e.g. SPA-PEG, SSPA-PEG, SBA-PEG, SS-PEG, SSA-PEG, SC-PEG, SG-PEG, and SCM-PEG), and NOR-PEG, BTC-PEG, EPDX-PEG, NCO-PEG, NPC-PEG, CDI-PEG, ALD-PEG, TRES-PEG, VS-PEG, IODO-PEG, and MAL-PEG, and branched PEGs such as PEG2-NHS.

The conjugation of the polypeptides or fusion proteins and the activated polymer molecules is conducted by use of any conventional method. Conventional methods are known to the skilled artisan. The skilled person will be aware that the activation method and/or conjugation chemistry to be used depends on the attachment group(s) of the polypeptides as well as the functional groups of the PEG molecule (e.g., being amine, hydroxyl, carboxyl, aldehyde, ketone, sulfhydryl, succinimidyl, maleimide, vinylsulfone or haloacetate).

In one embodiment, polypeptides are conjugated with PEGs at amino acid D and E (for COOH), T, Y and S (for OH), K (for NH2), C (for SH if at least one cysteine is conserved) or/and Q and N (for the amide function).

In one embodiment, additional sites for PEGylation can be introduced by site-directed mutagenesis by introducing one or more lysine residues. For instance, one or more arginine residues may be mutated to a lysine residue. In another embodiment, additional PEGylation sites are chemically introduced by modifying amino acids on polypeptides of the invention.

In one embodiment, PEGs are conjugated to the polypeptides or fusion proteins through a linker. Suitable linkers are well known to the skilled person. A preferred example is cyanuric chloride ((Abuchowski et al., 1977); U.S. Pat. No. 4,179,337).

Conventional separation and purification techniques known in the art can be used to purify pegylated polypeptides of the invention, such as size exclusion (e.g. gel filtration) and ion exchange chromatography. Products may also be separated using SDS-PAGE.

In one embodiment, the pegylated polypeptides provided by the invention have a serum half-life in vivo at least 50%, 75%, 100%, 150% or 200% greater than that of an unmodified polypeptide.

Nucleic Acids, Vectors and Recombinant Host Cells

A further object of the present invention relates to a nucleic acid sequence encoding for a polypeptide or a fusion protein according to the invention.

As used herein, a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

These nucleic acid sequences can be obtained by conventional methods well known to those skilled in the art.

Typically, said nucleic acid is a DNA or RNA molecule, which may be included in a suitable vector, such as a plasmid, cosmid, episome, artificial chromosome, phage or viral vector.

So, a further object of the present invention relates to a vector and an expression cassette in which a nucleic acid molecule encoding for a polypeptide or a fusion protein of the invention is associated with suitable elements for controlling transcription (in particular promoter, enhancer and, optionally, terminator) and, optionally, translation, and also the recombinant vectors into which a nucleic acid molecule in accordance with the invention is inserted. These recombinant vectors may, for example, be cloning vectors, or expression vectors.

As used herein, the terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

Any expression vector for animal cell can be used. Examples of suitable vectors include pAGE107 (Miyaji et al., 1990), pAGE103 (Mizukami and Itoh, 1987), pHSG274 (Brady et al., 1984), pKCR (O'Hare et al., 1981), pSG1 beta d2-4 (Miyaji et al., 1990) and the like.

Other examples of plasmids include replicating plasmids comprising an origin of replication, or integrative plasmids, such as for instance pUC, pcDNA, pBR, and the like.

Other examples of viral vectors include adenoviral, lentiviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. No. 5,882,877, U.S. Pat. No. 6,013,516, U.S. Pat. No. 4,861,719, U.S. Pat. No. 5,278,056 and WO 94/19478.

Examples of promoters and enhancers used in the expression vector for animal cell include early promoter and enhancer of SV40 (Mizukami and Itoh, 1987), LTR promoter and enhancer of Moloney mouse leukemia virus (Kuwana et al., 1987), promoter (Mason et al., 1985) and enhancer (Gillies et al., 1983) of immunoglobulin H chain and the like.

A further aspect of the invention relates to a host cell comprising a nucleic acid molecule encoding for a polypeptide or a fusion protein according to the invention or a vector according to the invention. In particular, a subject of the present invention is a prokaryotic or eukaryotic host cell genetically transformed with at least one nucleic acid molecule or vector according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

In a particular embodiment, for expressing and producing polypeptides or fusion proteins of the invention, prokaryotic cells, in particular *E. coli* cells, will be chosen. Actually, according to the invention, it is not mandatory to produce the polypeptide or the fusion protein of the invention in a eukaryotic context that will favour post-translational modifications (e.g. glycosylation). Furthermore, prokaryotic cells have the advantages to produce protein in large amounts. If a eukaryotic context is needed, yeasts (e.g. *saccharomyces* strains) may be particularly suitable since they allow production of large amounts of proteins. Otherwise, typical eukaryotic cell lines such as CHO, BHK-21, COS-7, C127, PER.C6, YB2/0 or HEK293 could be used, for their ability to process to the right post-translational modifications of the fusion protein of the invention.

The construction of expression vectors in accordance with the invention, and the transformation of the host cells can be carried out using conventional molecular biology techniques. The polypeptide or the fusion protein of the invention, can, for example, be obtained by culturing genetically transformed cells in accordance with the invention and recovering the polypeptide or the fusion protein expressed by said cell, from the culture. They may then, if necessary, be purified by conventional procedures, known in themselves to those skilled in the art, for example by fractional precipitation, in particular ammonium sulfate precipitation, electrophoresis, gel filtration, affinity chromatography, etc. In particular, conventional methods for preparing and purifying recombinant proteins may be used for producing the proteins in accordance with the invention.

A further aspect of the invention relates to a method for producing a polypeptide or a fusion protein of the invention comprising the step consisting of: (i) culturing a transformed host cell according to the invention under conditions suitable to allow expression of said polypeptide or fusion protein; and (ii) recovering the expressed polypeptide or fusion protein.

Therapeutic Methods and Uses

The polypeptide or the fusion protein of the invention may be used in a method of preventing or treating neurodegenerative disease in a subject in need thereof.

Therefore, a further aspect of the invention relates to the polypeptide or the fusion protein of the invention for use as a medicament.

In one embodiment, the present invention relates to the polypeptide or the fusion protein of the invention for use in the prevention or treatment of neurodegenerative disease in a subject in need thereof.

As used herein, the term "subject" denotes a mammal, such as a rodent, a feline, a canine, and a primate. Preferably a subject according to the invention is a human. Preferably a subject according to the invention is a subject afflicted or susceptible to be suffering from a neurodegenerative disease.

As used herein, the term "neurodegenerative disease" has its general meaning in the art and includes, but is not limited to Parkinson's disease, Alzheimer's disease and other dementias, Tauopathies, Amyotrophic lateral sclerosis (ALS; also known as motor neurone disease (MND) or Lou Gehrig's disease), Huntington's disease (HD), stroke, Aging neurodegeneration, Prion disease, Spinocerebellar ataxia (SCA), Spinal muscular atrophy (SMA), Alexander disease, Alper's disease, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, HIV-associated dementia, Kennedy's disease, Krabbe disease, Lewy body dementia, Machado-Joseph disease (Spinocerebellar ataxia type 3), Multiple sclerosis, Multiple System Atrophy, Neuroborreliosis, Pelizaeus-Merzbacher Disease, Pick's disease, Primary lateral sclerosis, Refsum's disease, Sandhoff disease, Schilder's disease, Sub-Acute Combined Degeneration of the Cord Secondary to Pernicious Anaemia, Schizophrenia, Spielmeyer-Vogt-Sjogren-Batten disease (also known as Batten disease), Steele-Richardson-Olszewski disease and Tabes dorsalis, dominant optical atrophy (DOA).

In some embodiments, the term "neurodegenerative disease" refers to neurodegenerative complications after ischemia damage. The term "neurodegenerative disease" also refers to neurodegenerative sequalae of ischemia.

As used herein, the term "ischemia damage" has its general meaning in the art and relates to any type of ischemia such as revised in the World Health Organisation Classification of ischemia and selected from the group: Cardiac ischemia, Ischaemic heart diseases (120-125 groups): Angina pectoris, Acute myocardial infarction, Subsequent myocardial infarction, Certain current complications following acute myocardial infarction (such as Haemopericardium, Atrial septal defect, Ventricular septal defect, Rupture of cardiac wall without haemopericardium, Rupture of chordae tendineae, Rupture of papillary muscle, Thrombosis of atrium, auricular appendage, and ventricle), Other acute ischaemic heart diseases (such as Coronary thrombosis not resulting in myocardial infarction and Dressler's syndrome), Chronic ischaemic heart disease (such as Atherosclerotic cardiovascular disease, Atherosclerotic heart disease, Old myocardial infarction, Ischaemic cardiomyopathy, Silent myocardial ischaemia); Brain ischemia, Transient cerebral ischaemic attacks and related syndromes (G45 group): Vertebro-basilar artery syndrome, Carotid artery syndrome (hemispheric), Multiple and bilateral precerebral artery syndromes, Amaurosis fugax, Transient global amnesia; Retinal ischemia; Kidney ischemia; intestinal ischemia; Limb ischemia; peripheral or diabetic-related ischemia; lung ischemia; liver ischemia; mesenteric ischemia; ischemia-reperfusion or ischemia-reperfusion organ damage.

In one embodiment, the present invention relates to the polypeptide or the fusion protein of the invention for use in the prevention of neurodegenerative complications in a subject suffering from ischemia damage.

In one embodiment, the present invention relates to the polypeptide or the fusion protein of the invention for use in the prevention of neurodegenerative sequalae of ischemia in a subject in need thereof.

In one embodiment, the present invention relates to the polypeptide or the fusion protein of the invention for use in the prevention or treatment of mitochondrial disease in a subject in need thereof.

As used herein, the term "mitochondrial disease" has its general meaning in the art and includes, but is not limited to mitochondrial myopathies, MELAS (mitochondrial encephalomyopathy, lactic acidosis, and stroke-like symptoms), MERRF (myoclonus, epilepsy with ragged red fibers), Pearson syndrome, Kearns-Sayre syndrome, Leigh syndrome, mitochondrial dysfunction in cardiomyocytes after ischemia damage, effects of ischemia to the cornea and retina, mitochondrial dysfunction such as in aging, glaucoma and other retinal disease including DOA (Dominant Optic Atrophy), mitochondrial dysfunction in kidney diseases, mitochondrial dysfunction in endothelial cells such as in atherosclerosis, diabetes mellitus, coronary artery disease, hypertension, and hypercholesterolemia, and mitochondrial diseases described in Osborne et al., 2014; O'Toole, 2014; Pagano et al., 2014; Zhan et al., 2013; Tang et al., 2014; WO 2012/019032; WO 2010/119344; WO 2014/011047 and WO 2005/033092.

In a particular embodiment, the polypeptide or the fusion protein of the invention may be administered sequentially or concomitantly with one or more therapeutic active agent such as anti-neurodegenerative agents.

Examples of anti-neurodegenerative agents include but are not limited to caspase inhibitors, energy boosters (such as carnitine or 1-creatine), antioxidants such as coenzyme Q10 (CoQ10) or azulenyl nitrone spin traps, inhibitors of neuronal nitric oxide synthase and cyclooxygenase 2, Cyclosporin A, SS (Szeto-Schiller) cell permeable synthetic tetrapeptides (such as Bendavia), and TPA (for cerebral ischemia degeneration).

A further aspect of the invention relates to a method for preventing or treating neurodegenerative disease in a subject in need thereof comprising the step of administering to said subject the polypeptide or the fusion protein of the invention.

A further aspect of the invention relates to a method for preventing or treating neurodegenerative complications in a subject suffering from ischemia damage comprising the step of administering to said subject the polypeptide or the fusion protein of the invention.

A further aspect of the invention relates to a method for preventing or treating mitochondrial disease in a subject in need thereof comprising the step of administering to said subject the polypeptide or the fusion protein of the invention.

Pharmaceutical Compositions

Another object of the invention relates to a pharmaceutical composition comprising the polypeptide or the fusion protein or the nucleic acid sequence or the expression vector or the host cell according to the invention and a pharmaceutically acceptable carrier.

Typically, the polypeptide or the fusion protein or the nucleic acid sequence or the expression vector or the host cell according to the invention may be combined with pharmaceutically acceptable excipients, and optionally sustained-release matrices, such as biodegradable polymers, to form therapeutic compositions.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention for intranasal, oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for intranasal instillation administration.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The polypeptide or fusion protein of the invention can be formulated into a composition in a neutral or salt form. Pharmaceutically acceptable salts include, but are not restricted to, the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small area.

Upon a formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

The peptide or the fusion protein of the invention may be formulated within a therapeutic mixture to comprise about 0.0001 to 1.0 milligrams, or about 0.001 to 0.1 milligrams, or about 0.1 to 1.0 milligrams, or about 1 to 10 milligrams or even about 10 to 100 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

Another object of the invention relates to a pharmaceutical composition according to the invention comprising one or more anti-neurodegenerative agents.

The invention will be further illustrated by the following figures and examples. However, these examples and figures should not be interpreted in any way as limiting the scope of the present invention.

FIGURES

FIG. 1: BDV protects against rotenone-induced axonal degeneration.

Quantification of axonal fragmentation, following rotenone treatment added either for 4 hours in the somatic chamber (+Rot soma), or for 16 hours in the axonal chamber (+Rot axon). Each point refers to the means of fragmentation indexes calculated for one microfluidic culture, in four independent experiments. ***: $p<0.001$, using Mann-Whitney test.

Figure 2:
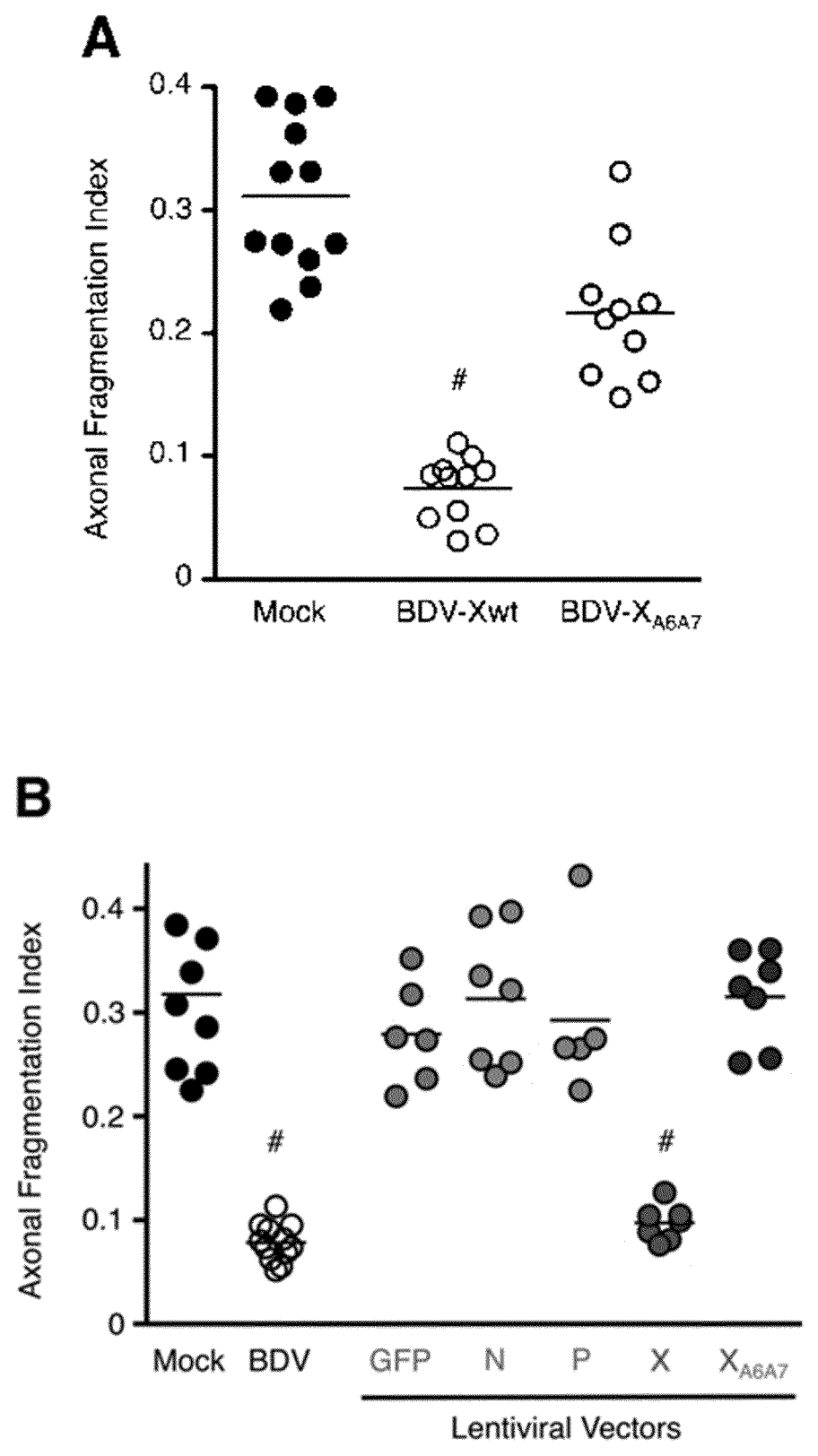

FIG. 2: Mitochondrial localization of X protein is necessary and sufficient to protect against rotenone-induced axonal fragmentation.

(A) Analysis of axonal fragmentation in mock-, rBDV-$X_{wt}$- or rBDV-$X_{A6A7}$-infected neurons grown in micro fluidic devices and treated with rotenone that was added in the axonal chamber for 16 h. Each point refers to the means of fragmentation indexes calculated for one microfluidic culture, in three independent experiments. (B) Analysis of axonal fragmentation in neurons transduced with lentiviral vectors expressing independently each indicated protein and treated with rotenone in the axonal chamber for 16 h. Each point refers to the means of fragmentation indexes calculated for one microfluidic culture, in three independent experiments. Differences were established by 1-way ANOVA. #: $p<10^{-4}$.

Figure 3:
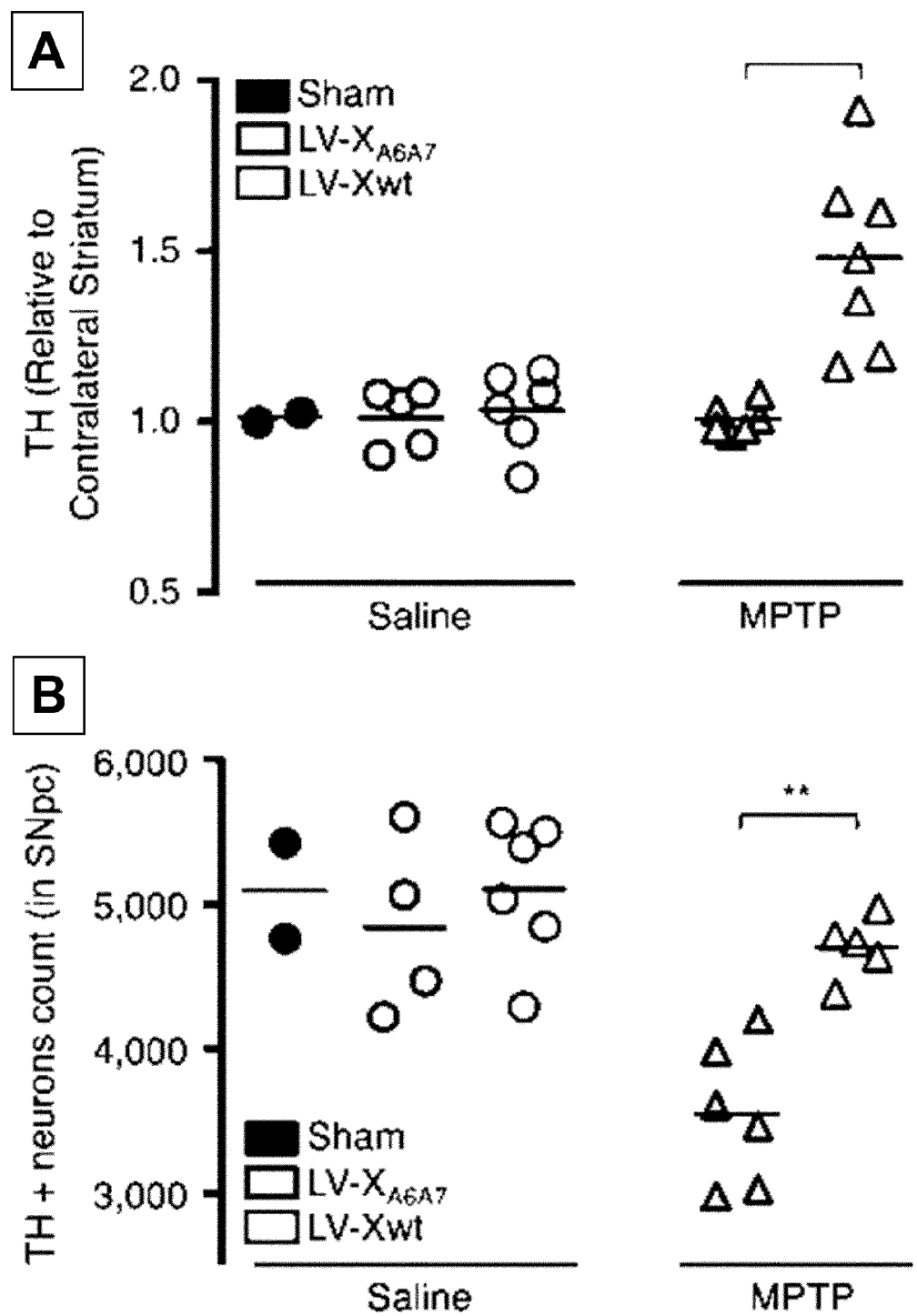

FIG. 3: X protein protects against DA system degeneration in the MPTP mouse model of PD.

(A) Quantification of striatal TH immunoreactivity (optical density). Data are expressed as ratios of optical density relative to the contralateral (non injected) side, i.e., any ratio>1 is indicative of neuroprotection. Each point represents one mouse. (B) Enumeration of surviving TH+ dopaminergic neurons in the ipsilateral SNpc. The horizontal bars represent the mean number of TH+ neurons. (Mann-Whitney test, : p<0.01; *: p<0.001).

FIG. 4: A peptide covering the carboxy-terminal 29 amino acids of X protein protects neurons from neurodegeneration.

(A) Design of peptides corresponding to different parts the X protein flanked by a mitochondrial targeting, cell-permeable sequence (MPP). (B) Analysis of rotenone-induced axonal fragmentation in mock-treated neurons or in neurons treated with the different peptides. Each point refers to the means of fragmentation indexes calculated for one microfluidic culture, from three independent experiments. Similar results were obtained with MPP+ (data not shown). (C-D) Impact of intranasal treatment with PX2 or PX3 peptides in the MPTP mouse model of PD. (C) Enumeration of surviving TH+ dopaminergic neurons in the SNpc. Each point represents one mouse. (D) Quantification of striatal TH immunoreactivity. Each point represents one mouse. (Mann-Whitney test, : p<0.01; *: p<0.001; 1 way ANOVA, ##: $p<10^{-4}$).

Figure 5:
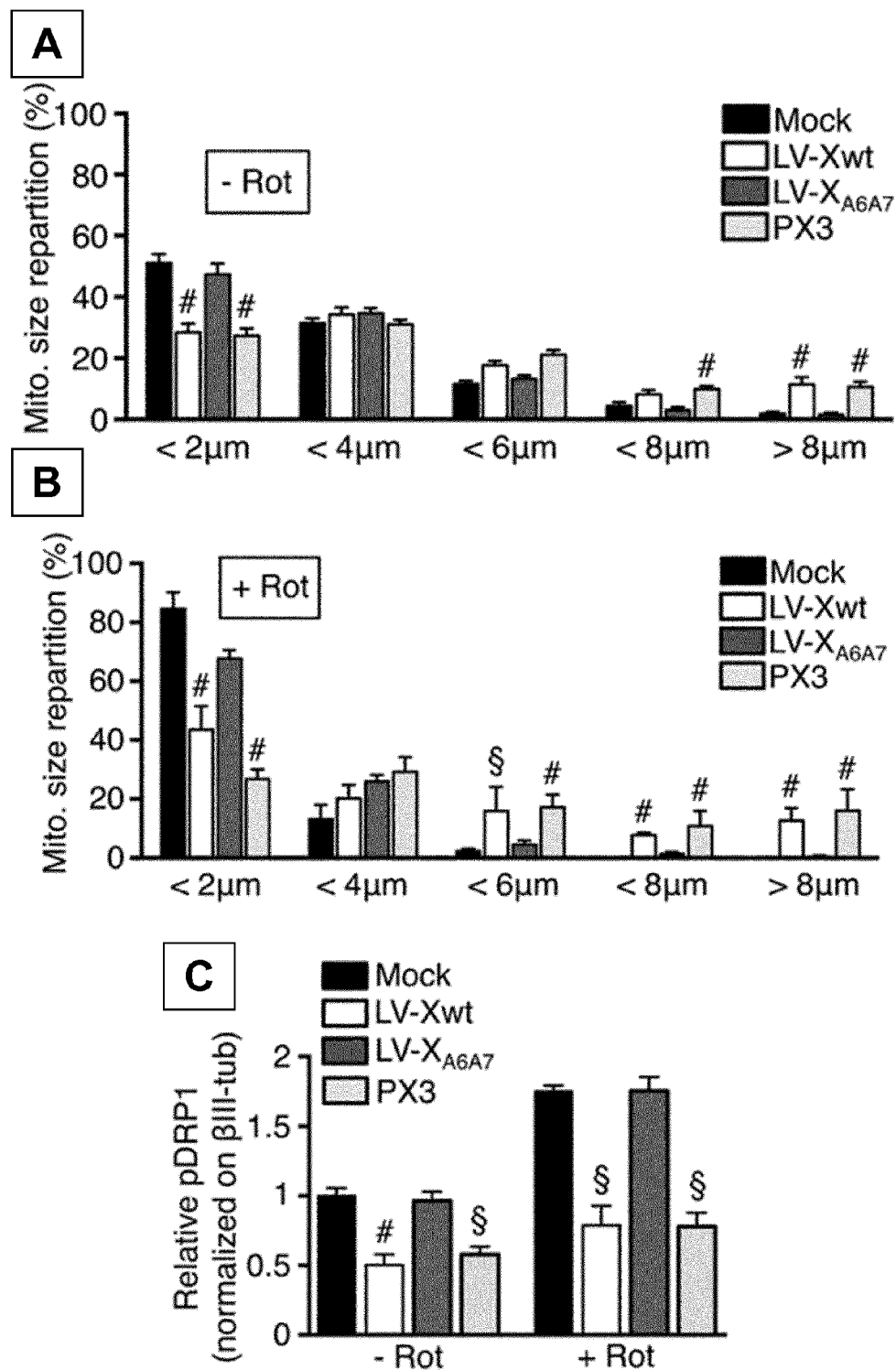

FIG. 5: The X protein triggers filamentation of the mitochondrial network, both at steady state and after oxidative stress, by blocking Drp1 (S616) phosphorylation.

(A-B) Mitochondria size repartitions were analyzed in control neurons (Mock), in neurons transduced with lentiviral vectors expressing either $X_{wt}$ (LV-X) or $X_{A647}$ (LV-$X_{A647}$), as well as in neurons treated with PX3 peptide. Analysis was performed without (−Rot, B) or after treating with 10 nM rotenone for 2 h (+Rot, C). Data were obtained from at least 15 neurons per group and per experiment. n=3 independent experiments. (C) Quantitative analysis of phospho-Drp1 (integrative intensity measurements using ImageJ software) showing that $X_{wt}$ protein or PX3 peptide block rotenone-induced Drp1 (S616) phosphorylation. Each value represents the mean of 3 randomly taken pictures, from 6 independent cultures (1 way ANOVA, #: $p<10^{-4}$; §: $p<10^{-3}$).

Figure 6:
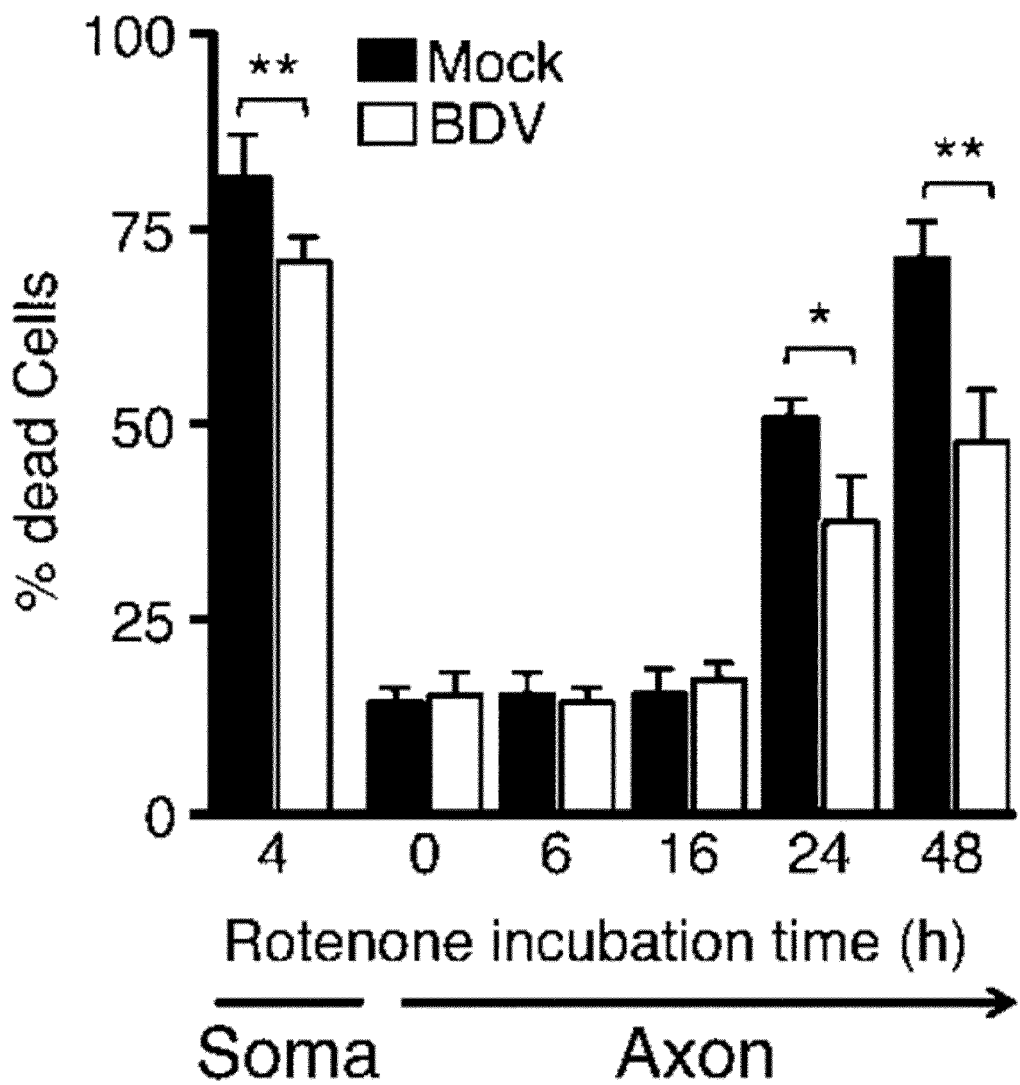

FIG. 6: Advantages of the microfluidic culture setting to model axonal dying back in cultured neurons.

Differences in the kinetics of neuronal death upon application of rotenone either in the somatodendritic (Soma) or in the axonal (Axon) chamber of microfluidic-based oriented primary neuronal cultures, either mock- or BDV-infected. Percentages of pyknotic nuclei were determined by TOPRO-3 staining at the indicated time points. n=4 independent experiments. Error bars indicate SEM. * p<0.05; ** p<0.01, using Mann-Whitney test.

Figure 7:
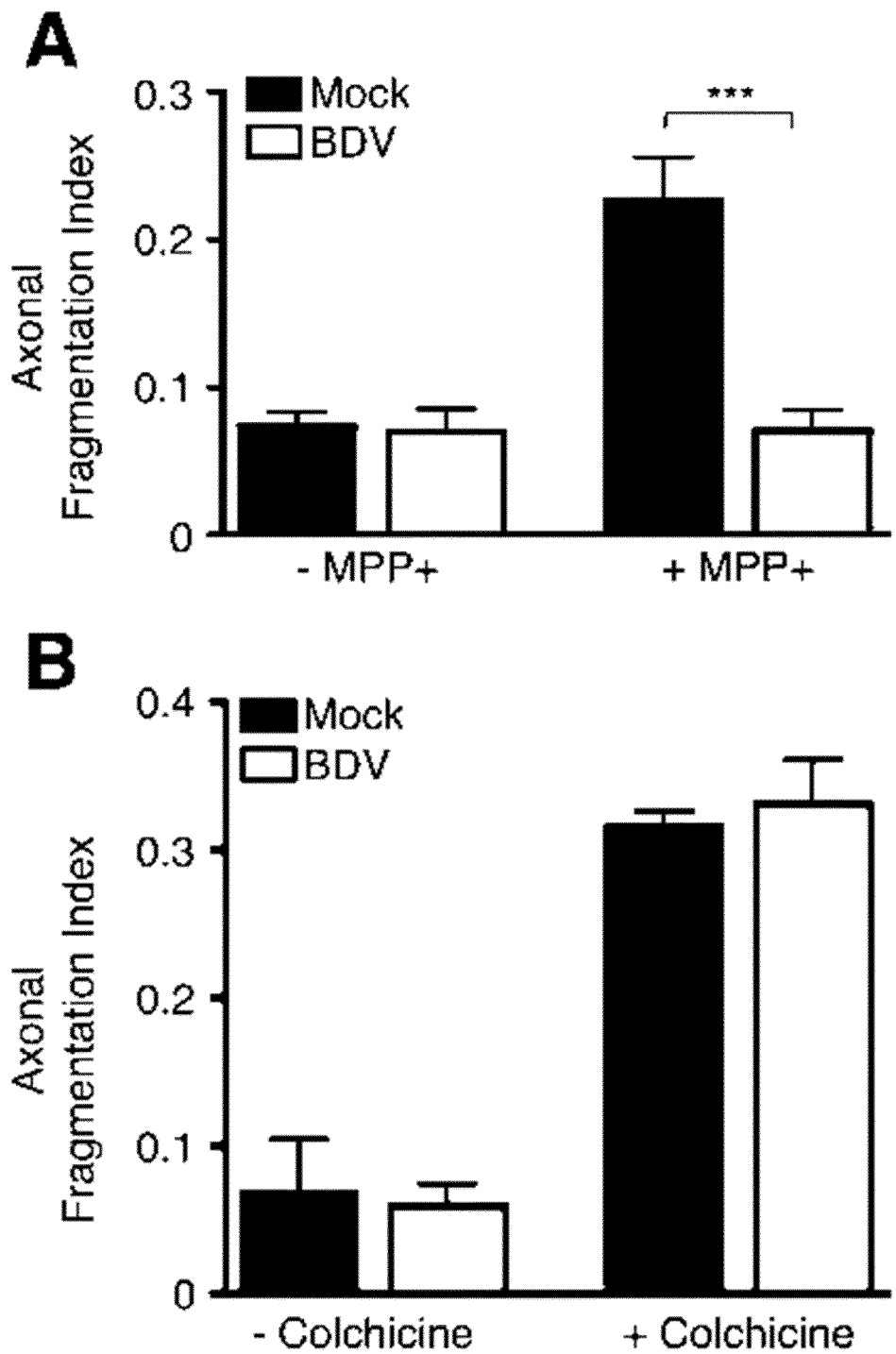

FIG. 7: BDV infection protects from axonal fragmentation induced by toxins that target the mitochondria but not against toxins that induce cytoskeleton damage.

Microfluidic-based oriented neurons cultures, either mock or BDV-infected, were treated by axonal application during 16 hours of (A) the respiratory complex I toxin MPP+ or (B) the tubulin polymerization inhibitor colchicine. Axonal fragmentation was determined as described in the methods. n=3 independent experiments (Statistics: Mann-Whitney test, *** p<0.001).

Figure 8:
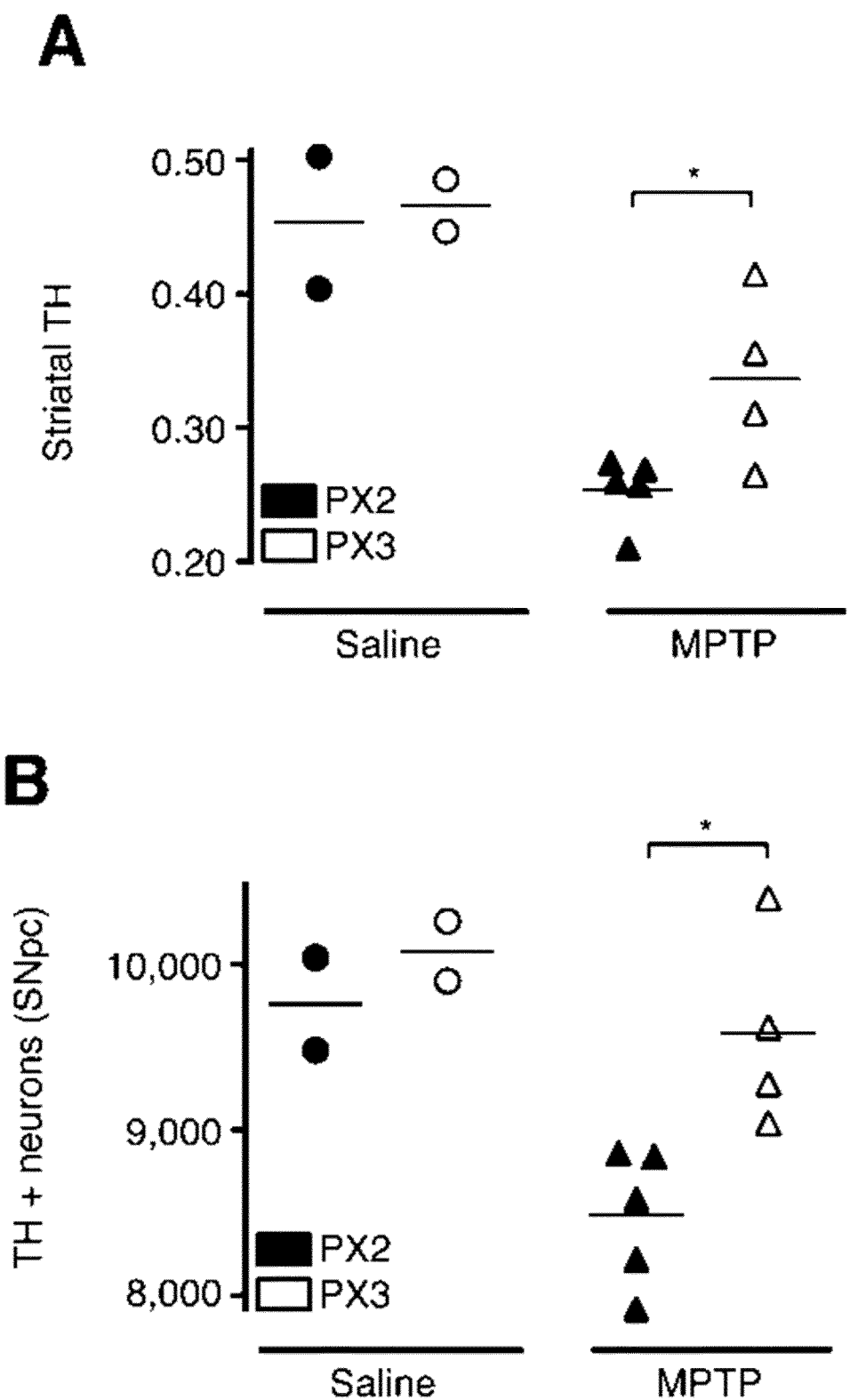

FIG. 8: Intra-cerebroventricular delivery of PX3, but not PX2 MPP-X peptide protects from MPTP-induced DA neuronal loss.

(A) Quantification of striatal TH immunoreactivity. (B) Quantification of TH+ dopaminergic neurons. (Mann-Whitney test, *p<0.05).

Figure 9:
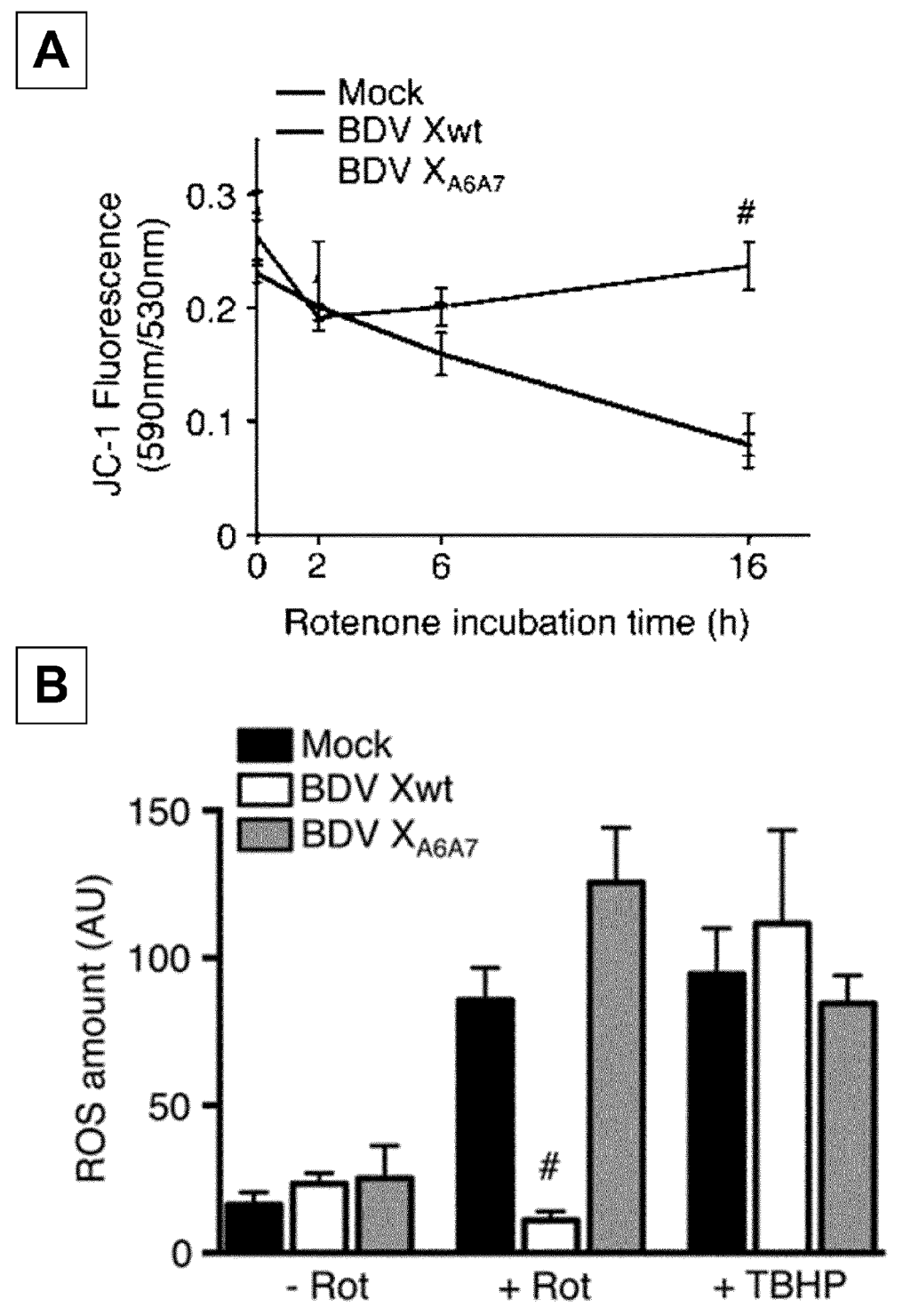

FIG. 9: BDV X protein protects from rotenone-induced oxidative stress.

(A-B) Analysis of ROS production (H2-CFDA probe) in the axonal chambers of microfluidic cultures of mock-, BDV-$X_{wt}$- and BDV-$X_{A647}$-infected neurons, before (−Rot) or 16 hours after axonal treatment with rotenone (+Rot). The positive control TBHP is also shown.

Figure 10:
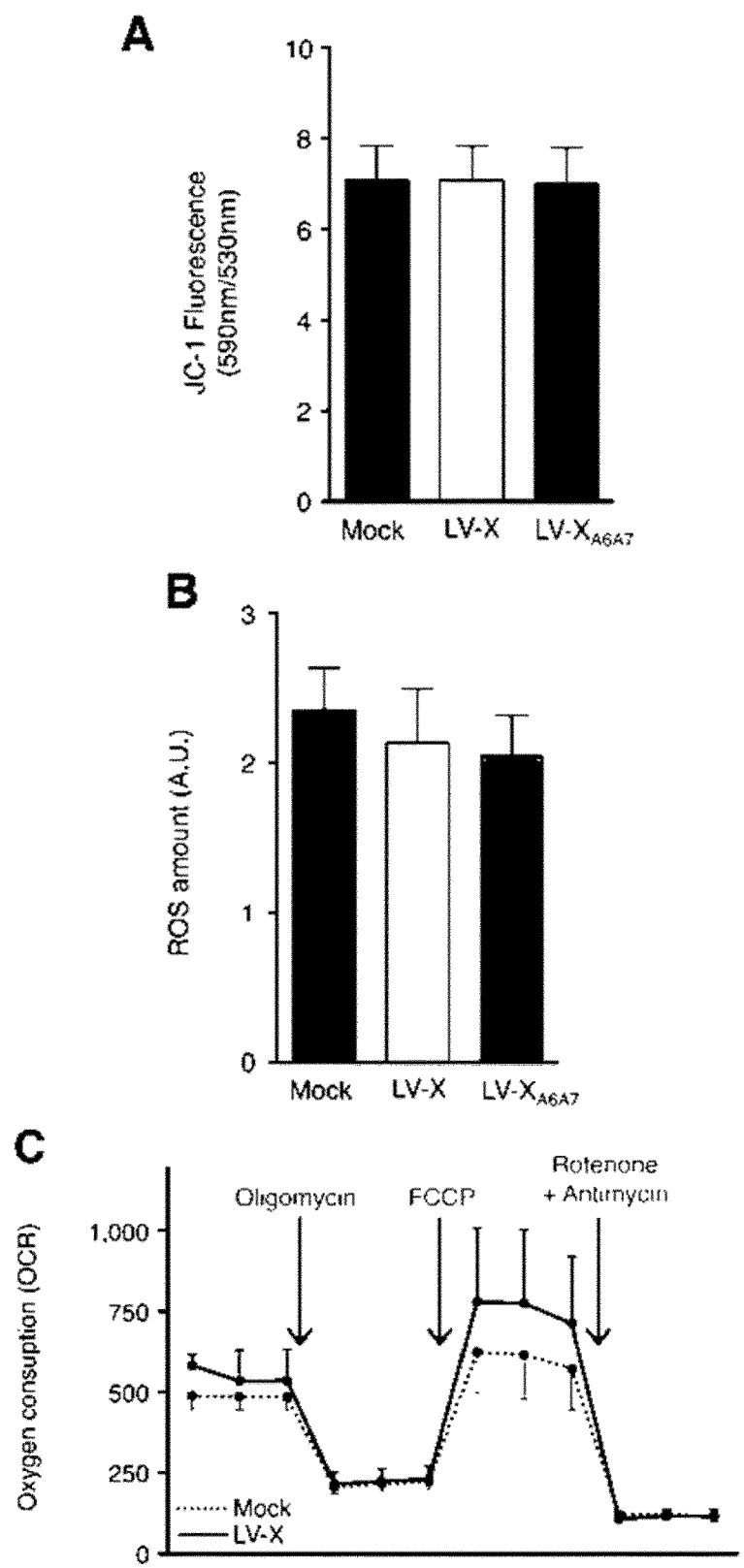

FIG. 10: BDV X protein has no impact on mitochondria physiology at steady state.

(A) Analysis of mitochondrial membrane potential (ΔΨm) using the JC-1 probe. (B) Analysis of ROS production using the H2D-CFDA probe. Measures were performed on primary neuronal cultures grown in 24-well plates, either mock-treated or transduced with LV-$X_{wt}$ or LV-$X_{A647}$ lentiviral vectors. (C) Real-time measurements of oxygen consumption rates (OCR) using a Seahorse XF24 extracellular flux analyzer. Neurons grown on XF24 specific plates were transduced with LV-$X_{wt}$ or with LV-GFP (as a control), 10 days before OCR analysis. Basal respiration and adaptability of the respiratory chain activity was assessed through the addition of different drugs in the culture medium during acquisition. OCR after Oligomycin represents the proton leak and the difference to basal respiration indicates the coupling efficiency for ATP production. Uncoupling by FCCP gives rise to maximal respiration, while treatment by Rotenone+Antimycin, which totally block mitochondrial respiration, indicate the non-mitochondrial part of neuronal respiration. Data are representative from 3 independent experiments.

EXAMPLE

Material & Methods

Ethics Statement

Animal experiments were performed following the French national chart for ethics of animal experiments (articles R 214-87 to 90 of the "Code rural"). Animals were housed, handled, and cared for in accordance with the European Union Council Directive 86/609/EEC. Our protocol received approval from the local committee on the ethics of animal experiments (permit number: 13CB-U1043 DD-11) and all efforts were made to minimize animal suffering.

Cells and Virus Strains

HEK 293T cells (ATCC CRL-3216) were passaged 1:8 twice a week in Dulbecco's Modified Eagle Medium (DMEM, Gibco) supplemented with 10% fetal calf serum (FCS, Gibco), 2 mM L-Glutamine (GE Healthcare) and 0.2 mg/ml Geneticin (Gibco). Cell-released virus stocks were prepared as described (42, 43), using Vero cells (ATCC CCL-81) infected with either BDV He/80 or recombinant viruses expressing wild type or mutated X (rBDV-LRD-$X_{wt}$ and rBDV-LRD-$X_{A647}$, a kind gift from U. Schneider, Freiburg University, Germany).

Primary cortical neurons were prepared from Sprague-Dawley rat embryos at gestational day 17. After dissection, cortex tissue was dissociated by a 15 min incubation at 37° C. in PBS containing 10 U/ml Papain (Worthington), followed by a gentle dissociation in PBS containing 1.5 mg/ml bovine serum albumin (BSA) and 1.5 mg/ml Trypsin inhibitor (from chicken egg, Sigma-Aldrich). After centrifugation through a 4% BSA cushion, neurons were plated on culture dishes coated with 0.5 mg/ml Poly-DL-Ornithine (PO, overnight, Sigma-Aldrich) and 5 mg/ml Laminin (2 h, Roche). Neuronal cultures were maintained in complete neuronal culture medium composed of serum-free Neurobasal (Gibco) supplemented with 2 mM L-Glutamine, 100 µg/ml penicillin/streptomycin (Gibco) and 2% B-27 supplement (Gibco).

Preparation of Microfluidic Culture Chambers and Neuronal Culture Setting

Microfluidic chips were prepared as described elsewhere (14, 15). Briefly, culture chambers were molded with polydimethylsiloxane (PDMS; Sylgard 184; Dow Corning, Midland, Mich., USA; 9:1 ratio with curing agent), which was poured into resin SU-8 silicon masters having a complementary positive relief pattern of the cell culture compartments and micro-channels. The resulting elastomeric polymer prints were detached and reservoirs were created using a biopsy puncher. After cleaning with isopropanol and air-drying, polymer prints and glass coverslips were treated for 1 min with an air plasma generator. Both elements were then bonded together, hydrated with sterile water, sterilized under UV for 15 min and coated with PO and Laminin. Primary neuronal cultures prepared as described above were adjusted to a final concentration of $5 \times 10^7$ cells/ml, and cell suspensions were seeded in the somatic chambers by introducing 3 µl in the upper reservoir. After 1 or 2 min, when neurons had attached to the substrate, reservoirs were filled with complete neuronal culture medium. A 10 µl differential medium volume was maintained between the somatic and axonal chambers to ensure a permanent hydrostatic flux. Neurons were infected with cell-free BDV (Giessen strain He/80, recombinant rBDV-LRD-$X_{wt}$ or -$X_{A6A7}$) one day after plating, or transduced with lentiviral vectors 3 days after plating.

Construction and Production of Lentiviral Vectors

The genes encoding BDV N (nucleoprotein), P (phosphoprotein), X, mutated $X_{A6A7}$ (7) or green fluorescent protein (GFP) were amplified by PCR and cloned into pTrip vector (kind gift from Dr. P. Charneau, Pasteur Institute, Paris) using BamHI and XhoI restriction sites, downstream the constitutive cytomegalovirus (CMV) enhancer/chicken ß-actin (CAG) promoter. To produce the lentiviral vectors, 10 T150 flasks plated with $1.2 \times 10^7$ HEK-293T cells each were transfected with packaging plasmids psPAX2, pMD2.G (both from Addgene) and pTrip expressing the different genes (respectively 14.6 µg, 7.9 µg, 22.5 µg of endotoxin-free prepared plasmids mixed with 100 µl of GeneJuice (Merck) for each T150). Culture medium was removed the next day and replaced by warm OptiMEM (Gibco). Supernatant was collected 48 h and 72 h post transfection, cleared by low-speed centrifugation, filtered using a 0.45 µm filter and lentiviral particles were purified by ultracentrifugation through a 20% sucrose cushion (25,000 rpm, 2 h, 4° C.; SW32Ti rotor, Beckman Coulter). Ice-cold PBS was added to each centrifugation tube and lentivector-containing pellets were let to swell under gentle agitation overnight at 4° C., prior to being recovered, aliquoted and stored à −80° C. Lentivector titers were determined by counting foci 72 h after transduction of HEK-293T cells with serial dilutions. In all our experiments, titers varied from $8 \times 10^8$ to $3 \times 10^9$ transduction units (TU)/ml and were used at a multiplicity of transduction of 5 (transduction units of vector per cell) for in vitro neuronal transduction.

Induction of Axonal or Somatic Oxidative Stress 12 day-old neuronal cultures were subjected to oxidative stress by adding the respiratory chain complex I inhibitors rotenone (1 µM, diluted in DMEM containing 1 g/L glucose (Invitrogen), supplemented with 2 mM glutamine+1% penicillin/streptomycin+2% B-27+1% N2 supplements (Invitrogen)) or MPP+(1-methyl-4-phenylpyridinium, 10 µM in complete neuronal culture medium). The microtubule inhibitor colchicine (10 µM, complete neuronal culture medium) was used as a non-mitochondrial stress control. Toxins were added in the somatic or axonal chambers for respectively, somatic or axonal stress.

Immunofluorescence and Imaging in Microfluidic Chambers

Neurons in the microfluidic cultures were fixed for 40 min at room temperature with PBS containing 4% paraformaldehyde (PFA), permeabilized using PBS+0.1% Triton-X100 during 20 min, rinsed with PBS, and blocked for 2 h with PBS+2.5% normal goat serum+3% BSA (blocking buffer). Incubation for at least 2 h at room temperature with primary antibodies diluted in blocking buffer was followed, after extensive washes in PBS, by 1 h incubation at room temperature with fluorescently-conjugated secondary antibodies diluted in PBS. For TOPRO3 staining, somatic chambers were incubated with TOPRO3 (1:1000 in PBS; Invitrogen) for 10 min and then rinsed twice in PBS. All incubation and washes were reduced by 50% for neurons grown in standard coverslips. Fluorescence-based analyses and measurements were performed on either Zeiss LSM-510 or Zeiss LSM-710 inverted confocal microscopes with a 40× objective (63× objective for the analysis of mitochondrial network morphology and quantification of pDrp1 (S616) immunoreactivity). Immuno fluorescence analyses of Drp1 were performed using anti-pDrp1 (S616) (Cell Signaling Technologies, diluted 1:1000). Quantification of fluorescence intensities was performed using the threshold-based fluorescence quantification module of ImageJ software. All data were normalized on βIII-tubulin staining.

Analysis of Axonal Fragmentation

The analysis of axonal degeneration was performed both by phase contrast observation and after immunostaining of axonal βIII-tubulin (Sigma-Aldrich). Intact axons present a linear phase contrast morphology and an homogeneous tubulin staining delineating the axon shaft, while blebbed or severed axons exhibit a fragmented morphology and punctate tubulin network. For each microfluidic culture, the total βIII-tubulin staining area was measured on 4 randomly selected pictures taken in the axonal chamber (MetaMorph software analysis, fixed thresholds). Then, the number of tubulin spots of fragmented axons was manually counted (Imaris software, Spot counting for "clicking" records) and the ratio between the number of spots and the total staining area was defined as a fragmentation index.

To control for infection or transduction efficiencies, immunostaining for BDV antigens (using homemade rabbit antisera raised against N, P or X proteins) were performed together with βIII-tubulin. To ensure that the hydrostatic flux had indeed prevented drugs from diffusing back to the somas through the channels, TOPRO3 (Invitrogen) staining was performed in somatic chambers and nuclear integrity was checked for each culture. The observation of more than 25% fragmented/dead nuclei in control or axonal-damaged cultures was an exclusion criterion.

Synthesis and Use of X-Derived Peptides

Peptides covering the N-terminal (PX1, aa 1-30), middle (PX2, aa 29-59) or C-terminal (PX3, aa 59-87) parts of BDV X protein (GenBank: ABW81015.1) coupled to the MPP sequence were synthesized to >95% (in vitro studies) or >99% (in vivo studies) purity (Génosphère). For in vitro experiments, neurons were grown for 12 days before replacing the medium by fresh complete neuronal culture medium containing 5 µM of the peptides. The cultures were maintained 90 min at 37° C., 5% $CO_2$ before any treatment or analysis to ensure peptide penetration into neuronal mitochondria. For intra-cerebroventricular delivery, peptides were injected as described below. For intranasal peptide delivery, 10 µl drops of peptide solution (1 mM solution in saline: $H_2O+0.9\%$ NaCl) were placed onto the mice nostrils daily from the day before to the $3^{rd}$ day after MPTP intoxication.

Stereotaxic Surgery

Unilateral stereotaxic injection of lentiviral vectors were performed into the Substantia Nigra pars compacta (SNpc) of 8 week-old mice at the following coordinates: AP −2.6 mm relative to Bregma, ML+1.2 mm, and DV −4.4 mm from the dura. Each mouse was injected with $1.10^6$ transduction units of vectors in a volume of 1 µl at the flow rate of 0.1 µl/min using a 10 µl microsyringe (Hamilton). Mice were rested post-operation for 2 weeks before MPTP intoxication.

For the intra-cerebroventricular (ICV) delivery of peptides, cannulas (Phymep) were stereotaxically implanted into the lateral ventricle through a hole drilled in the skull at the following coordinates: AP 0.0 mm relative to Bregma, ML+1.0 mm, and DV −2.0 mm from skull. Dental cement was used to fix the cannula guide to the skull (polycarboxylate, Sigma, France) and to prevent occlusion. Mice were rested post-operation for 2 weeks before peptide delivery and subsequent MPTP intoxication. Peptide was injected through the cannulas by fixation of an injector (Phymep) connected to a peristaltic pump, the day before and every day for 3 days after intoxication (2 nmol in 2 µl per injection, injection rate: 0.5 µl/min).

MPTP Intoxication and Tissue Processing

For 1-Methyl-4-phenyl-1,2,3,6-tetrahydropyridine (MPTP) intoxication, mice were injected i.p. four times at 2 h intervals with either 18.5 mg/kg MPTP-HCl (as free base), or a corresponding volume of 0.9% NaCl solution. Mice were kept for 3 weeks to ensure lesion stabilization prior to sacrifice. Mice were anesthetized with a mixture of ketamine hydrochloride (100 mg/kg, i.p.) and xylazine (15 mg/kg, i.p.) dissolved in isotonic saline sterile solution, or with sodium pentobarbital (150 mg/kg, i.p.) and transcardiacally perfused at a flow rate of 5 ml/min with PBS (20 ml) followed by ice-cold 4% PFA (100 ml). After extraction from the skull, brains were further post-fixed overnight in fresh 4% PFA solution, and cryoprotected with 30% sucrose in Phosphate buffer. Brains were then frozen by immersion in −30° C. isopentane and kept at −80° C. until further processing. Series of striatal and mesencephalic coronal sections (20-µm thick) were collected using a freezing microtome (Thermo Scientific) and stored in PBS containing 0.3% sodium azide.

Immunohistochemistry Analysis

For immunohistochemical staining, free-floating brain sections were first quenched for 5 min in 20% (v/v) methanol and 1% (v/v) hydrogen peroxide diluted in PBS, then blocked for 30 min in a 4% solution of BSA diluted in PBS-0.3% Triton-X100 and incubated overnight at 4° C. with a primary antibody directed against tyrosine hydroxylase (1:500 dilution, US biological). After extensive washing in PBS, the sections were incubated for 1 h with biotinylated secondary antibody (1:250 dilution; Vector Laboratories). Staining was visualized by the ABC method (Vector Laboratories) with 3,3-diaminobenzidine (DAB) as the peroxydase substrate. TH-positive neurons were quantified stereologically on regularly spaced sections covering the whole Substantia Nigra pars compacta (SNpc). The SNpc was delineated as previously described (44) and TH-positive cell bodies were counted by bright-field microscopy, using a Leitz microscope equipped with image analysis software (Mercator, ExploraNova, La Rochelle, France). Striatal TH optic densitometry were quantified using the MCID software (MCID analysis 7.0). Staining background measured in the cerebral cortex was subtracted from striatal density measurements. The investigator performing the quantification was blinded to the treatment groups during the whole analysis process.

Mitochondrial Membrane Potential Analysis

Axons were stained with JC-1 dye (2 µM in PBS; LifeTechnologies) as described by the manufacturer. Briefly, JC-1 was added to the culture medium for 45 min at 37° C., 5% $CO_2$, washed twice with PBS and analyzed by confocal microscopy using 488 nm excitation together with 530 nm and 585 nm band pass emission filters, whilst maintaining the cells at 37° C. and 5% $CO_2$. Total fluorescence intensity was measured for each emission band pass with fixed thresholds and ratios between "red" (585 nm: active mitochondria) and "green" (530 nm: total mitochondria network) were determined for each culture (means of 4 randomly chosen pictures for each microfluidic culture).

ROS Production Measurement

The culture medium was removed from the axonal or somatic chambers and replaced by pre-warmed PBS containing carboxy-2',7'-dichlorodihydrofluorescein diacetate (c-H2DCFDA, 5 µM in PBS; LifeTechnologies) for 45 min at 37° C., 5% $CO_2$. After 2 washes in PBS, cultures were returned to warm culture medium for 30 min. Cells were fixed and the integrative fluorescence was measured on 3 randomly selected fields for each axonal chamber. Tert-butyl hydroperoxide (TBHP, LifeTechnologies) was used as a positive control of ROS detection. ROS amounts were detected by fluorescence (excitation/emission: 495/529 nm) and quantified by measuring integrative emission signal intensities for each culture (mean of 4 randomly taken pictures in the case of microfluidic cultures using Zeiss LSM 510 confocal; signal intensity of the whole culture for traditional cultures, using a VarioSkan Flash fluorescence reader (Thermo Electron)).

Analysis of Mitochondrial Network Morphology

Neurons were grown for 9 days at low density on 12 mm diameter glass coverslips placed in 24-well plates ($5 \times 10^4$ cells per well). Transduction with lentiviral vectors was performed on day 3, whereas peptide was added to the medium on day 9. Neurons were left untreated or subjected to rotenone treatment (5 to 100 nM for 2 h, diluted in PBS), rinsed, fixed and directly stained for neuronal marker (βIII-tubulin) and mitochondria (Tom20, Santa Cruz Biotech.). Confocal pictures were taken and blinded to the investigator before image analysis. The sizes of mitochondria in all neuronal extensions of randomly selected neurons were determined using ImageJ software and mitochondria were classified in size categories (ranging from <2 µm to >8 µm). Each category was expressed as percentages relative to the size of the total mitochondrial network for a given neuron.

Mitochondrial Respiration Measurements

Real-time measurements of oxygen consumption rates (OCR) were performed using a Seahorse XF24 extracellular flux analyzer (Seahorse Bioscience). Neurons were seeded and grown for 9 days in Seahorse XF24-wells plates ($3 \times 10^4$ cells/well). Transduction with lentiviral vectors was performed on the 3rd day after seeding. Before measurements, the culture medium was replaced by warm respiration medium: DMEM without phenol red supplemented with 10 mM glucose, 2 mM L-Glutamine and 2 mM Pyruvate (Gibco) (the pH of the final culture medium was adjusted to 7.4). Following three 2-minute baseline measurements of OCR (3 minute-rest between each measure), mitochondrial complex inhibitors were sequentially injected into each well. Three OCR readings were taken after addition of each inhibitor and before automated injection of the subsequent inhibitor. Mitochondrial complex inhibitors, in order of injection, were Oligomycin (2 μM) to inhibit complex V (i.e., ATP synthase), FCCP (20 μM) to uncouple the proton gradient, Rotenone (2.0 μM), to inhibit complex I and Antimycin (2.0 μM), to inhibit complex III. OCR values were automatically calculated, recorded, and plotted by the Seahorse XF24 software.

Results

The progressive loss of structure and function of neurons in neurodegenerative diseases, such as PD, involves mitochondrial dysfunction and axonal degeneration (1, 2). Despite considerable efforts, we still lack efficient therapies to block neuronal demise in the early stages of neurodegeneration. Viruses, as obligatory parasites, have evolved highly specific means to hijack cellular pathways. In order to optimize the survival in their host, many viruses express proteins, or non-coding RNA, that block or delay the death of infected cells by acting at the mitochondrial level (3-5). In particular, some neurotropic viruses have very efficient strategies to protect neurons, given that their target cells have a very poor capacity of renewal. A case in point is Bornavirus (or BDV), a highly neurotropic RNA virus that persists in the brain of many animal species without causing direct damage to neurons (6). BDV non-cytolytic replication is due to the expression of an 87 amino acids viral protein called X that targets mitochondria in the infected cells (7). Here, the inventors investigated the possibility that the X protein could protect neurons against neurodegenerative insults, even when used outside of the viral context. In particular, the inventors assessed protection against mitochondrial respiratory complex I toxins, which induce oxidative stress and neurodegeneration in tissue culture and in animal models (8-11).

Neuronal loss in neurodegenerative diseases usually proceeds through a protracted dying-back pattern in which dysfunction of nerve endings and axonal demise long precedes neuronal cell body destruction (1). The inventors therefore reasoned that neurotropic viruses that need axons to spread in the CNS might have developed potent strategies to prevent axonal degeneration (13). Thus, the inventors used primary neuron cultures in micro fluidic devices, which permit strict separation of the axonal and somatodendritic compartments and allow assessing the neuroprotective efficacy of BDV infection (14-16). As previously described, somatic application of the complex I inhibitor rotenone led to rapid (<4 h) cell death, whereas axonal application of rotenone triggered progressive axonal degeneration preceding somatic cell destruction (FIG. 6), illustrating the advantages of this setup to model the dying back pattern of neurodegeneration (17, 18). Strikingly, when rotenone was applied to axons, the inventors observed that BDV infection almost entirely abrogated axonal fragmentation (FIG. 1). A similar protection against axonal fragmentation was observed after axonal treatment with MPP+, the active form of 1-methyl-4-phenyl-1,2,3,6-tetrahydropyridine (MPTP), another complex I toxin that induces oxidative stress and which is widely used to model PD-like neurodegeneration in rodents and primates (19) (FIG. 7A). Rotenone and MPP+ toxins act on mitochondria but also inhibit tubulin assembly. To distinguish between both activities, the inventors used colchicine, which inhibits microtubule polymerization by binding to tubulin. Infection did not protect against colchicine-induced axonal fragmentation (FIG. 7B), showing that BDV infection specifically protects axons from complex I inhibition.

To assess the role of BDV X protein interaction with mitochondria in axonal protection, the inventors next compared the protective effects of infection with recombinant wild-type BDV (BDV-$X_{wt}$) and a recombinant BDV in which the X protein had been mutated (7) to abrogate its mitochondrial localization (BDV-$X_{A6A7}$). Consistent with the results shown above, infection with BDV-$X_{wt}$ strongly protected axons against rotenone-induced fragmentation. In contrast, there was no protection with BDV-$X_{A6A7}$ (FIG. 2A). To test whether BDV X protein could exhibit neuroprotection by itself, the inventors constructed lentiviral vectors (LV) expressing GFP (as a control) and various BDV proteins: the nucleoprotein (N), the phosphoprotein (P), protein $X_{wt}$ or the $X_{A6A7}$ mutant that is no longer targeted to the mitochondria. Neurons grown in microfluidic devices were transduced with the different LV and axonal fragmentation was assayed after 16 h of rotenone treatment of axons. Expression of wild type X alone conferred the same level of axonal protection as infection with BDV (FIG. 2B). None of the other viral proteins induced protection and using the $X_{A6A7}$ mutant showed that the mitochondrial localization of the X protein was required for axonal protection.

The inventors then tested the neuroprotective properties of the X protein in vivo using the MPTP intoxication mouse model of PD (20-22). Lentiviral vectors expressing either wild type (LV-X) or its non-mitochondrial targeted mutant (LV-$X_{A6A7}$) were introduced by stereotaxic injection in the Substantia Nigra pars compacta (SNpc), two weeks before MPTP intoxication. The survival of nigrostriatal dopaminergic (DA) neurons was assayed by tyrosine hydroxylase (TH) immunodetection in the striatum (axonal projections) or SNpc (cell bodies). MPTP-intoxicated mice receiving the mutated X protein showed a marked loss of TH-positive neurons (FIG. 3). In contrast, mice receiving the wild type X protein were remarkably protected against MPTP toxicity, with a preservation of ipsilateral striatal fibers (injected side, FIG. 3A) and an almost complete protection of ipsilateral TH-positive neurons in the SNpc (FIG. 3D).

Despite these encouraging results, stereotaxic injection of neuroprotective compounds is invasive and cannot be envisioned as a therapy (23, 24). Therefore, the inventors asked whether small cell-permeable peptides derived from the X protein could exhibit similar properties and be neuroprotective following systemic administration. The inventors interrogated the structure of the X protein in an attempt to identify a neuroprotective domain. Computer analysis of the X protein did not reveal any homology with other viral or cellular proteins. In silico structure modeling predicted a globally disordered protein, except for a short N-terminal aliphatic alpha helix, which carry both nuclear and mitochondrial localization domains and thus did not point to obvious sequence that may be responsible for neuroprotection (25, 26). Thus, the inventors synthesized three peptides covering the entire X protein to test each separately for neuroprotection (FIG. 4A). To ensure their targeting to mitochondria, the inventors coupled them with a mitochondria-penetrating peptide sequence (SEQ ID NO:3: F-R-Cha-K-F-R-Cha-K, Cha=cyclohexylalanine), originally derived from the cell-penetrating HIV tat peptide and which was recently shown to allow both plasma membrane crossing and mitochondria targeting with high specificity (27, 28). This sequence has successfully been used to deliver small covalently bound molecules to mitochondria (29, 30). The inventors first confirmed that fusing this sequence to the X-derived peptides allowed their mitochondrial accumulation within 90 minutes of adding them in the culture medium of primary neurons. The inventors next assayed neuroprotection against rotenone-induced axonal fragmentation using their microfluidic neuronal culture model. Remarkably, peptide PX3, corresponding to the C-terminal part of the X protein (FIG. 4A), provided protection similar to that of full-length X protein. The other peptides did not exhibit any protection (FIG. 4B), suggesting that the neuroprotective property of the X protein resides entirely within its 29 amino acid C-terminal sequence.

The inventors next examined if PX3 could be protective in the MPTP mouse model of PD. Intra-cerebroventricular injection of this peptide led to 40% and 53% protection against MPTP-induced loss of striatal and SNpc TH-positive neurons, respectively (FIG. 8). In order to explore a more convenient systemic route of administration, the inventors then performed intranasal (i.n.) instillations of the peptide. Indeed, the i.n. route is known to bypass the blood-brain barrier and target therapeutic agents to the central nervous system (31). Moreover, i.n. delivery of MPTP is effective in modeling PD in mice, demonstrating the ability of chemicals to get from the olfactive bulb to the nigrostriatal pathway (32). Since dopaminergic neuronal insult occurs mainly within the first 4 days after acute MPTP intoxication (20), the inventors delivered the peptides i.n. daily, one day before i.p. MPTP intoxication and during the following four days. In the control group, which received the PX2 peptide instead of PX3, mice displayed a marked loss of TH-positive neurons (FIG. 4C) and striatal dopaminergic fibers (FIG. 4D). Strikingly, when mice received the PX3 peptide, the lesions were reduced by 40%, both in SNpc and striatum (FIG. 4C-D).

The underlying mechanism of protection conferred by the X protein and PX3 against mitochondrial poisoning was investigated further. Both rotenone and MPP+ block the formation of the electrochemical gradient across the inner mitochondrial membrane (ΔΨm) (33, 34). In the axonal compartment of microfluidic neuronal cultures, the inventors observed that $X_{wt}$, but not the $X_{A647}$ mutated virus prevented the time-dependent loss of ΔΨm triggered by rotenone exposure (FIG. 9). Likewise, wild type BDV also prevented rotenone-induced oxidative stress and burst of ROS production (FIG. 9). Together, these data show that the X protein is able to buffer mitochondrial dysfunctions triggered by complex I toxins and to preserve neurons from the resulting oxidative stress. Interestingly, expression of X had no impact on mitochondrial parameters (ΔΨm, ROS production and respiration) at steady-state (FIG. 10) but only preserved mitochondria integrity when neurons were subjected to oxidative stress.

Mitochondrial network dynamics plays a major role in mitochondria quality control and has emerged as a central actor in neurodegeneration (35, 36). Generally, the mitochondrial network becomes fragmented in response to stress and a filamentous network ensures a better response to oxidative stress, both through dilution of stress molecules and compensatory mechanisms (37, 38). The inventors thus analyzed mitochondrial morphology in neurons expressing X, $X_{A647}$ or treated with PX3 peptide, both at steady state and after rotenone-induced oxidative stress. At steady state, the presence of X or PX3 resulted in a more filamentous network (weighted mean sizes=5.22 μm and 5.07 μm, respectively, vs. 3.27 μm in control neurons and 3.00 μm in neurons expressing $X_{A647}$), with a 60% decrease of short, fragmented mitochondria (<2 μm) and a 4 to 5 fold increase in long mitochondria (>8 μm) (FIG. 5A). Importantly, the X protein or PX3 peptide significantly reduced rotenone-induced mitochondrial fission (FIG. 5B) and preserved the presence of mitochondria under long forms (weighted mean size=4.54 μm and 4.87 μm, respectively, vs. 2.31 μm in control neurons and 2.38 μm in neurons expressing $X_{A647}$).

To investigate the underlying mechanism of the hyper filamentation of the mitochondrial network induced by the X protein, the inventors tested whether it had an impact on the expression and/or activation of mitochondrial fission/fusion actors. The inventors did not find any significant difference in the expression levels of the fusion proteins Optical Atrophy 1 (OPA1) and mitofusins 1 and 2 (Mfn1/2), or in the fission actors Fis1 or Dynamin-related protein 1 (Drp1) between control and X-expressing cells. Likewise, there was no difference in the recruitment of Drp1 to the mitochondria. Strikingly, phosphorylation of Drp1 on its serine-616 residue, which participates in mitochondrial fission (39) was severely reduced in X protein- or PX3-expressing neurons, but not when using the non-mitochondrial $X_{A647}$ mutant (FIG. 5C). Moreover, the enhanced Drp1 phosphorylation observed after treatment with rotenone was also selectively reduced in X protein- or PX3-expressing neurons (FIG. 5C), which might underlie their preservation of a filamentous mitochondrial network.

Thus, considering the growing evidence of the role of mitochondrial dynamics in neurodegeneration (40, 41), these findings show that the X protein and the PX3 peptide target a major culprit in neurodegeneration. These virus-derived peptides therefore define a new class of neuroprotective agents with great potential for the treatment of patients suffering from PD or other neurodegenerative diseases.

REFERENCES

Throughout this application, various references describe the state of the art to which this invention pertains. The disclosures of these references are hereby incorporated by reference into the present disclosure.

1. M. Filosto et al., The role of mitochondria in neurodegenerative diseases. J. Neurol. 258, 1763 (October, 2011).
2. A. Johri, M. F. Beal, Mitochondrial dysfunction in neurodegenerative diseases. J. Pharmacol. Exp. Ther. 342, 619 (September, 2012).
3. L. Galluzzi, C. Brenner, E. Morselli, Z. Touat, G. Kroemer, Viral control of mitochondrial apoptosis. Plos Pathog 4, e1000018 (May, 2008).
4. M. B. Reeves, A. A. Davies, B. P. McSharry, G. W. Wilkinson, J. H. Sinclair, Complex I binding by a virally encoded RNA regulates mitochondria-induced cell death. Science 316, 1345 (Jun. 1, 2007).
5. W. L. Kuan et al., A novel neuroprotective therapy for Parkinson's disease using a viral noncoding RNA that protects mitochondrial Complex I activity. J. Exp. Med. 209, 1 (Jan. 16, 2012).
6. W. I. Lipkin, T. Briese, M. Hornig, Borna disease virus—Fact and fantasy. Virus Res., (Oct. 1, 2011).
7. M. Poenisch, N. Burger, P. Staeheli, G. Bauer, U. Schneider, Protein X of Borna disease virus inhibits apoptosis and promotes viral persistence in the central nervous systems of newborn-infected rats. J Virol 83, 4297 (May, 2009).
8. W. J. Nicklas, I. Vyas, R. E. Heikkila, Inhibition of NADH-linked oxidation in brain mitochondria by 1-methyl-4-phenyl-pyridine, a metabolite of the neurotoxin, 1-methyl-4-phenyl-1,2,5,6-tetrahydropyridine. Life Sci. 36, 2503 (Jul. 1, 1985).
9. W. J. Nicklas, S. K. Youngster, M. V. Kindt, R. E. Heikkila, MPTP, MPP+ and mitochondrial function. Life Sci. 40, 721 (Feb. 23, 1987).
10. N. Exner, A. K. Lutz, C. Haass, K. F. Winklhofer, Mitochondrial dysfunction in Parkinson's disease:

molecular mechanisms and pathophysiological consequences. Embo J 31, 3038 (Jul. 18, 2012).
11. J. T. Greenamyre, T. B. Sherer, R. Betarbet, A. V. Panov, Complex I and Parkinson's disease. IUBMB life 52, 135 (September-November, 2001).
12. J. C. Vickers et al., Axonopathy and cytoskeletal disruption in degenerative diseases of the central nervous system. Brain Res. Bull. 80, 217 (2009).
13. I. Tsunoda, T. Tanaka, E. J. Terry, R. S. Fujinami, Contrasting roles for axonal degeneration in an autoimmune versus viral model of multiple sclerosis: When can axonal injury be beneficial? Am. J. Pathol. 170, 214 (January, 2007).
14. D. Kilinc et al., Wallerian-like degeneration of central neurons after synchronized and geometrically registered mass axotomy in a three-compartment micro fluidic chip. Neurotox Res 19, 149 (January, 2011).
15. S. Magnifico et al., NAD+ acts on mitochondrial SirT3 to prevent axonal caspase activation and axonal degeneration. Faseb J, (Aug. 23, 2013).
16. B. Deleglise et al., Synapto-protective drugs evaluation in reconstructed neuronal network. PLoS ONE 8, e71103 (2013).
17. H. Bernheimer, W. Birkmayer, O. Hornykiewicz, K. Jellinger, F. Seitelberger, Brain dopamine and the syndromes of Parkinson and Huntington. Clinical, morphological and neurochemical correlations. J. Neurol. Sci. 20, 415 (December, 1973).
18. M. C. Raff, A. V. Whitmore, J. T. Finn, Axonal self-destruction and neurodegeneration. Science 296, 868 (May 3, 2002).
19. M. Herkenham et al., Selective retention of MPP+ within the monoaminergic systems of the primate brain following MPTP administration: an in vivo autoradiographic study. Neuroscience 40, 133 (1991).
20. V. Jackson-Lewis, S. Przedborski, Protocol for the MPTP mouse model of Parkinson's disease. Nature protocols 2, 141 (2007).
21. S. Przedborski, M. Vila, The 1-methyl-4-phenyl-1,2,3,6-tetrahydropyridine mouse model: a tool to explore the pathogenesis of Parkinson's disease. Ann N Y Acad Sci 991, 189 (June, 2003).
22. J. Bove, C. Perier, Neurotoxin-based models of Parkinson's disease. Neuroscience 211, 51 (Jun. 1, 2012).
23. J. Luo et al., Subthalamic GAD gene therapy in a Parkinson's disease rat model. Science 298, 425 (Oct. 11, 2002).
24. T. F. Outeiro et al., Sirtuin 2 inhibitors rescue alpha-synuclein-mediated toxicity in models of Parkinson's disease. Science 317, 516 (Jul. 27, 2007).
25. M. Poenisch, S. Wille, U. Schneider, P. Staeheli, Second-site mutations in Borna disease virus overexpressing viral accessory protein X. J Gen Virol 90, 1932 (August, 2009).
26. T. Wolff, G. Unterstab, G. Heins, J. A. Richt, M. Kann, Characterization of an unusual importin alpha binding motif in the borna disease virus p10 protein that directs nuclear import. J Biol Chem 277, 12151 (2002).
27. L. F. Yousif, K. M. Stewart, K. L. Horton, S. O. Kelley, Mitochondria-penetrating peptides: sequence effects and model cargo transport. Chembiochem: a European journal of chemical biology 10, 2081 (Aug. 17, 2009).
28. L. E. Marbella, H. S. Cho, M. M. Spence, Observing the translocation of a mitochondria-penetrating peptide with solid-state NMR. Biochim. Biophys. Acta 1828, 1674 (August, 2013).
29. M. P. Pereira, S. O. Kelley, Maximizing the therapeutic window of an antimicrobial drug by imparting mitochondrial sequestration in human cells. J. Am. Chem. Soc. 133, 3260 (Mar. 16, 2011).
30. L. F. Yousif, K. M. Stewart, S. O. Kelley, Targeting mitochondria with organelle-specific compounds: strategies and applications. Chembiochem: a European journal of chemical biology 10, 1939 (Aug. 17, 2009).
31. L. R. Hanson, W. H. Frey, 2nd, Intranasal delivery bypasses the blood-brain barrier to target therapeutic agents to the central nervous system and treat neurodegenerative disease. BMC neuroscience 9 Suppl 3, S5 (2008).
32. J. Franco et al., Antioxidant responses and lipid peroxidation following intranasal 1-methyl-4-phenyl-1,2,3,6-tetrahydropyridine (MPTP) administration in rats: increased susceptibility of olfactory bulb. Life Sci. 80, 1906 (Apr. 24, 2007).
33. E. Hasegawa, K. Takeshige, T. Oishi, Y. Murai, S. Minakami, 1-Methyl-4-phenylpyridinium (MPP+) induces NADH-dependent superoxide formation and enhances NADH-dependent lipid peroxidation in bovine heart submitochondrial particles. Biochem. Biophys. Res. Commun. 170, 1049 (Aug. 16, 1990).
34. E. Hasegawa et al., A dual effect of 1-methyl-4-phenylpyridinium (MPP+)-analogs on the respiratory chain of bovine heart mitochondria. Arch. Biochem. Biophys. 337, 69 (Jan. 1, 1997).
35. T. Tatsuta, T. Langer, Quality control of mitochondria: protection against neurodegeneration and ageing. Embo J 27, 306 (Jan. 23, 2008).
36. E. I. Rugarli, T. Langer, Mitochondrial quality control: a matter of life and death for neurons. Embo J 31, 1336 (Mar. 21, 2012).
37. K. Itoh, K. Nakamura, M. Iijima, H. Sesaki, Mitochondrial dynamics in neurodegeneration. Trends Cell Biol 23, 64 (February, 2013).
38. R. J. Youle, A. M. van der Bliek, Mitochondrial fission, fusion, and stress. Science 337, 1062 (Aug. 31, 2012).
39. N. Taguchi, N. Ishihara, A. Jofuku, T. Oka, K. Mihara, Mitotic phosphorylation of dynamin-related GTPase Drp1 participates in mitochondrial fission. J Biol Chem 282, 11521 (Apr. 13, 2007).
40. A. B. Knott, G. Perkins, R. Schwarzenbacher, E. Bossy-Wetzel, Mitochondrial fragmentation in neurodegeneration. Nat Rev Neurosci 9, 505 (July, 2008).
41. X. Guo et al, Inhibition of mitochondrial fragmentation diminishes Huntington's disease-associated neurodegeneration. J. Clin. Invest., (Nov. 15, 2013).
42. J. J. Bajramovic et al., Borna disease virus glycoprotein is required for viral dissemination in neurons. J Virol 77, 12222 (November, 2003).
43. A. Hans et al., Persistent, noncytolytic infection of neurons by Borna disease virus interferes with ERK 1/2 signaling and abrogates BDNF-induced synaptogenesis. Faseb J 18, 863 (May, 2004).
44. D. C. German et al., The neurotoxin MPTP causes degeneration of specific nucleus A8, A9 and A10 dopaminergic neurons in the mouse. Neurodegeneration 5, 299 (December, 1996).
45. D. W. Buchan, F. Minneci, T. C. Nugent, K. Bryson, D. T. Jones, Scalable web services for the PSIPRED Protein Analysis Workbench. Nucleic Acids Res. 41, W349 (July, 2013).
46. Burbulla, L. F., et al. Dissecting the role of the mitochondrial chaperone mortalin in Parkinson's disease:

functional impact of disease-related variants on mitochondrial homeostasis. Hum. Mol. Genet. 19, 4437-4452 (2010).
47. Jin, J., et al. Identification of novel proteins associated with both alpha-synuclein and DJ-1. Mol Cell Proteomics 6, 845-859 (2007).
48. Shi, M., et al. Mortalin: a protein associated with progression of Parkinson disease? J. Neuropathol. Exp. Neurol. 67, 117-124 (2008).
49. Osborne N N1, Alvarez C N2, Del Olmo Aguado S2. Targeting mitochondrial dysfunction as in aging and glaucoma. Drug Discov Today. 2014 May 28.
50. O'Toole J F. Renal manifestations of genetic mitochondrial disease. Int J Nephrol Renovasc Dis. 2014 Jan. 31; 7:57-67.
51. Pagano G, Aiello Talamanca A, Castello G, Cordero M D, d'Ischia M, Gadaleta M N, Paliaró F V, Petrović S, Tiano L, Zatterale A. Oxidative Stress and Mitochondrial Dysfunction across Broad-Ranging Pathologies: Toward Mitochondria-Targeted Clinical Strategies. Oxid Med Cell Longev. 2014; 2014:541230.
52. Tang X, Luo Y X, Chen H Z, Liu D P. Mitochondria, endothelial cell function, and vascular diseases. Front Physiol. 2014 May 6; 5:175.
53. Zhan Ml, Brooks C, Liu F, Sun L, Dong Z. Mitochondrial dynamics: regulatory mechanisms and emerging role in renal pathophysiology. Kidney Int. 2013 April; 83(4): 568-81.

The invention claimed is:

1. A fusion protein comprising
   I) a polypeptide comprising
      i) an amino acid sequence ranging from glycine at position 59 to alanine at position 85 in an amino acid sequence SEQ ID NO:1 or,
      ii) an amino acid sequence having at least 90% identity with the amino acid sequence ranging from glycine at position 59 to alanine at position 85 in the amino acid sequence SEQ ID NO:1,
      wherein the polypeptide consists of 86 amino acids or less; and
   II) at least one heterologous polypeptide fused to the polypeptide.

2. The fusion protein of claim 1 wherein the heterologous polypeptide is a cell-penetrating peptide.

3. The fusion protein of claim 1 wherein the heterologous polypeptide is a Transactivator of Transcription (TAT) cell penetrating sequence SEQ ID NO:2, or a mitochondria-penetrating peptide sequence SEQ ID NO:3.

4. A nucleic acid sequence encoding a fusion protein comprising
   I) a polypeptide comprising
      i) an amino acid sequence ranging from glycine at position 59 to alanine at position 85 in an amino acid sequence SEQ ID NO:1 or,
      ii) an amino acid sequence having at least 90% identity with the amino acid sequence ranging from glycine at position 59 to alanine at position 85 in the amino acid sequence SEQ ID NO:1,
      wherein the polypeptide consists of 86 amino acids or less; and
   II) at least one heterologous polypeptide.

5. A vector comprising a nucleic acid sequence encoding a fusion protein comprising
   I) a polypeptide comprising
      i) an amino acid sequence ranging from glycine at position 59 to alanine at position 85 in an amino acid sequence SEQ ID NO:1 or,
      ii) an amino acid sequence having at least 90% identity with the amino acid sequence ranging from glycine at position 59 to alanine at position 85 in the amino acid sequence SEQ ID NO:1,
      wherein the polypeptide consists of 86 amino acids or less; and
   II) at least one heterologous polypeptide.

6. A prokaryotic or eukaryotic host cell genetically transformed with at least one nucleic acid molecule encoding a fusion protein comprising
   I) a polypeptide comprising
      i) an amino acid sequence ranging from glycine at position 59 to alanine at position 85 in an amino acid sequence SEQ ID NO:1 or,
      ii) an amino acid sequence having at least 90% identity with the amino acid sequence ranging from glycine at position 59 to alanine at position 85 in the amino acid sequence SEQ ID NO:1,
      wherein the polypeptide consists of 86 amino acids or less; and
   II) at least one heterologous polypeptide; or
   a vector comprising the nucleic acid.

7. A pharmaceutical composition comprising
   a pharmaceutically acceptable carrier; and
   a fusion protein comprising
   I) a polypeptide comprising
      i) an amino acid sequence ranging from glycine at position 59 to alanine at position 85 in an amino acid sequence SEQ ID NO:1 or,
      ii) an amino acid sequence having at least 90% identity with the amino acid sequence ranging from glycine at position 59 to alanine at position 85 in the amino acid sequence SEQ ID NO:1,
      wherein the polypeptide consists of 86 amino acids or less; and
   II) at least one heterologous polypeptide.

8. A recombinant polypeptide comprising
   i) an amino acid sequence ranging from glycine at position 59 to alanine at position 85 in an amino acid sequence SEQ ID NO:1 or,
   ii) an amino acid sequence having at least 90% identity with the amino acid sequence ranging from glycine at position 59 to alanine at position 85 in the amino acid sequence SEQ ID NO:1, wherein the polypeptide consists of 86 amino acids or less.

9. The recombinant polypeptide of claim 8, wherein said polypeptide is conjugated with at least one polyethylene glycol group.

10. A vector comprising a nucleic acid sequence encoding
    I) a polypeptide comprising
       i) an amino acid sequence ranging from glycine at position 59 to alanine at position 85 in an amino acid sequence SEQ ID NO:1 or,
       ii) an amino acid sequence having at least 90% identity with the amino acid sequence ranging from glycine at position 59 to alanine at position 85 in the amino acid sequence SEQ ID NO:1,
       wherein the polypeptide consists of 86 amino acids or less.

11. A prokaryotic or eukaryotic host cell genetically transformed with at least one nucleic acid molecule encoding
    I) a recombinant polypeptide comprising
       i) an amino acid sequence ranging from glycine at position 59 to alanine at position 85 in an amino acid sequence SEQ ID NO:1 or,
       ii) an amino acid sequence having at least 90% identity with the amino acid sequence ranging from glycine at position 59 to alanine at position 85 in the amino acid sequence SEQ ID NO:1,
wherein the polypeptide consists of 86 amino acids or less.

12. A pharmaceutical composition comprising
a pharmaceutically acceptable carrier; and
I) a recombinant polypeptide comprising
   i) an amino acid sequence ranging from glycine at position 59 to alanine at position 85 in an amino acid sequence SEQ ID NO:1 or,
   ii) an amino acid sequence having at least 90% identity with the amino acid sequence ranging from glycine at position 59 to alanine at position 85 in the amino acid sequence SEQ ID NO:1,
wherein the polypeptide consists of 86 amino acids or less.

13. The pharmaceutical composition of claim 12 further comprising an anti-neurodegenerative agent.

* * * * *

SEQUENCE LISTING

```
<160> NUMBER OF SEQ ID NOS: 3

<210> SEQ ID NO 1
<211> LENGTH: 87
<212> TYPE: PRT
<213> ORGANISM: Borna disease virus

<400> SEQUENCE: 1

Met Ser Ser Asp Leu Arg Leu Thr Leu Leu Glu Leu Val Arg Arg Leu
1               5                   10                  15

Asn Gly Asn Ala Thr Ile Glu Ser Gly Arg Leu Pro Gly Gly Arg Arg
            20                  25                  30

Arg Ser Pro Asp Thr Thr Thr Gly Thr Val Gly Val Thr Lys Thr Thr
        35                  40                  45

Glu Asp Pro Lys Glu Cys Ile Asp Pro Thr Gly Arg Pro Ala Pro Glu
    50                  55                  60

Gly Pro Gln Glu Glu Pro Leu His Asp Leu Arg Pro Arg Pro Ala Asn
65                  70                  75                  80

Arg Lys Gly Ala Ala Ile Glu
                85

<210> SEQ ID NO 2
<211> LENGTH: 12
<212> TYPE: PRT
<213> ORGANISM: Artificial
<220> FEATURE:
<223> OTHER INFORMATION: Synthetic Transactivator of Transcription (TAT)
      cell penetrating sequence

<400> SEQUENCE: 2

Gly Arg Lys Lys Arg Arg Gln Arg Arg Arg Pro Gln
1               5                   10

<210> SEQ ID NO 3
<211> LENGTH: 8
<212> TYPE: PRT
<213> ORGANISM: Artificial
<220> FEATURE:
<223> OTHER INFORMATION: Synthetic Mitochondria-penetrating peptide
      sequence
<220> FEATURE:
<221> NAME/KEY: VARIANT
<222> LOCATION: (3)..(3)
```

```
<223> OTHER INFORMATION: Xaa=Cha=cyclohexylalanine
<220> FEATURE:
<221> NAME/KEY: VARIANT
<222> LOCATION: (7)..(7)
<223> OTHER INFORMATION: Xaa=Cha=cyclohexylalanine

<400> SEQUENCE: 3

Phe Arg Xaa Lys Phe Arg Xaa Lys
1               5
```